(12) United States Patent
Burgess et al.

(10) Patent No.: US 12,390,358 B2
(45) Date of Patent: Aug. 19, 2025

(54) SYSTEMS AND METHODS FOR DISPOSABLE URINALS

(71) Applicant: Medline Industries, LP, Springfield, IL (US)

(72) Inventors: James E. Burgess, Lake Bluff, IL (US); Kristopher J. Ivie, Hallam, PA (US)

( * ) Notice: Subject to any disclaimer, the term of this patent is extended or adjusted under 35 U.S.C. 154(b) by 429 days.

(21) Appl. No.: 18/080,679

(22) Filed: Dec. 13, 2022

(65) Prior Publication Data

US 2024/0189137 A1 Jun. 13, 2024

(51) Int. Cl.
A61F 5/453 (2006.01)
A61F 5/44 (2006.01)
A61F 5/455 (2006.01)

(52) U.S. Cl.
CPC ............ *A61F 5/453* (2013.01); *A61F 5/455* (2013.01); *A61F 2005/4402* (2013.01)

(58) Field of Classification Search
CPC ... A61F 5/453; A61F 5/455; A61F 2005/4402
See application file for complete search history.

(56) References Cited

U.S. PATENT DOCUMENTS

| | | |
|---|---|---|
| D37,300 S | 1/1905 | Meinecke |
| 1,440,765 A * | 1/1923 | Buckley ............... A61F 5/44 4/144.1 |
| D212,516 S | 10/1968 | Beich et al. |
| D245,267 S | 8/1977 | Gruber |
| D248,168 S | 6/1978 | Kelly |
| D249,076 S | 8/1978 | Meeker et al. |
| D297,462 S | 8/1988 | Meunchen |
| 5,343,570 A * | 9/1994 | Arpaia ................ A61G 7/0503 4/144.1 |
| D371,842 S | 7/1996 | Pilsworth |
| D389,240 S | 1/1998 | Corona |
| D399,308 S | 10/1998 | Garlock |
| 5,926,858 A * | 7/1999 | Heller ................. A47K 11/12 4/144.1 |
| 6,026,519 A * | 2/2000 | Kaluza ................ A61G 9/006 4/144.1 |
| D578,211 S * | 10/2008 | Maze .......................... D24/122 |
| D771,803 S * | 11/2016 | Tanguay ...................... D24/122 |
| D832,425 S * | 10/2018 | Adams, III .................. D24/122 |
| D950,716 S * | 5/2022 | Schweizer ................... D24/122 |
| D977,630 S | 2/2023 | Smith |
| 2009/0158511 A1 | 6/2009 | Maze et al. |
| 2015/0320628 A1 * | 11/2015 | Sands ..................... A61F 5/453 4/144.3 |
| 2024/0189137 A1 * | 6/2024 | Burgess ................ A61F 5/455 |
| 2024/0315866 A1 * | 9/2024 | Garlock ................ A61F 5/441 |

* cited by examiner

*Primary Examiner* — Guy K Townsend
(74) *Attorney, Agent, or Firm* — Quarles & Brady LLP

(57) ABSTRACT

A urinal can include a body defining a front end, a rear end opposite the front end, and an internal volume. The body can include an opening fluidly coupled to the internal volume of the body and positioned at the front end of the body. The urinal can include a handle integrally formed with the body. The handle can have a free end that can extend away from the front end of the body towards the rear end of the body. The urinal can include a recess directed into a bottom end of the body. The recess can be configured to receive a second handle of a second urinal.

34 Claims, 15 Drawing Sheets

SYSTEMS AND METHODS FOR DISPOSABLE URINALS

CROSS-REFERENCE TO RELATED APPLICATIONS

Not applicable.

STATEMENT REGARDING FEDERALLY SPONSORED RESEARCH

Not applicable.

BACKGROUND

Disposable urinals are typically used in healthcare facilities to allow patients to void urine without having to physically travel to a restroom. For example, after surgery, other procedures, etc., patients may be unable to physically move to a restroom, or partitioners (e.g., doctors) may impose strict movement restrictions on patients for a period of time after a procedure, each of which limits the ability of a patient to physically go to a restroom. Thus, disposable urinals can not only allow patients to remotely void urine but can also allow patients to void urine in a much more hygienic manner than other solutions.

In some cases, disposable urinals are preformed and are packed in a container to be shipped to a healthcare facility, stored at the healthcare facility, etc. However, there can be considerable inefficiencies with packing (and thus shipping) cases of disposable urinals. Thus, it would be desirable to have improved systems and methods for disposable urinals.

SUMMARY OF THE DISCLOSURE

Some non-limiting examples of the disclosure provide a urinal. The urinal can include a body defining a front end, a rear end opposite the front end, and an internal volume. The body can include an opening fluidly coupled to the internal volume of the body and positioned at the front end of the body. The urinal can include a handle integrally formed with the body. The handle can have a free end that can extend away from the front end of the body towards the rear end of the body. The urinal can include a recess directed into a bottom end of the body. The recess can be configured to receive a second handle of a second urinal.

In some non-limiting examples, a recess can include a first portion and a second portion. The first portion can be positioned closer to a rear end of a body than the second portion. A second handle of a second urinal can include a base and an arm extending away from the base. The first portion of the recess can be configured to receive the arm of the second handle and the second portion of the recess can be configured to receive the base of the second handle.

In some non-limiting examples, an internal volume of a handle can be fluidly coupled to an internal volume of a body.

In some non-limiting examples, a recess of a urinal can correspond in shape to a second handle of a second urinal. When the second handle of the second urinal is inserted into the recess of the urinal, at least a portion of the urinal outside of a recess can be configured to contact the second urinal.

In some non-limiting examples, a body can include an extension. A free end of the extension can extend away from a rear end of the body and towards a front end of the body. The extension can at least partially define a recess of the urinal.

In some non-limiting examples, an internal volume of a body can extend into an extension to define an extension internal volume. The extension internal volume can be configured to contain a liquid.

In some non-limiting examples, a longitudinal axis can bisect at least a portion of a body to define a first side of the body and a second side of the body. The longitudinal axis can extend through a front end and a rear end of the body. At least a portion of a recess, a portion of a extension, a portion of a handle, or a center of an opening can be only positioned on the first side of the body.

In some non-limiting examples, a portion of a recess, a portion of an extension, a portion of a handle, and a center of an opening can be only positioned on a first side of a body.

In some non-limiting examples, an entire handle, and an entire recess can be positioned on only a first side of a body.

In some non-limiting examples, a body can include a seam that can define a ridge that can extend across at least a portion of the body, a portion of a handle, a portion of the body at an opening, a portion of an extension, a portion of the body at a recess, and a portion of the body outside of the opening and the recess.

In some non-limiting examples, a body can include a neck that can join an opening. The neck can be curved or can be angled upwardly relative to a longitudinal axis.

In some non-limiting examples, a recess can be a first recess and an opening can be a first opening. A neck can include a second recess that can be directed into the neck. A second urinal at a second opening of the second urinal can be configured to be inserted within the second recess when a second handle of the second urinal is received within a first recess.

In some non-limiting examples, a urinal can include a third recess directed into a neck. A second recess can be positioned above the third recess. A second urinal can include a loop proximal to a second opening that can be configured to receive a tether. The loop of the urinal can be configured to be inserted into the third recess of the urinal when a second handle of the second urinal is received within a first recess.

In some non-limiting examples, a rear end of a body can be angled upwardly relative to a longitudinal axis of the body.

In some non-limiting examples, a body can include a first side wall and a second side wall opposite the first side wall. The first side wall can include a raised portion and a substantially flat portion. The raised portion can be configured to be compressed to align with the substantially flat portion and decrease an internal volume of a body. The raised portion can be configured to expand from being compressed and extend away from the substantially flat portion to increase the internal volume of the body.

In some non-limiting examples, a substantially flat portion can surround a raised portion.

In some non-limiting examples, a raised portion can span at least 50% of an entire area of a first side wall.

In some non-limiting examples, a raised portion can contour a shape of a body along the body.

In some non-limiting examples, a urinal can include indicia that can indicate an amount of liquid positioned within an internal volume of a body of the urinal. The indicia can be positioned on a raised portion.

In some non-limiting examples, a front end and a rear end can be curved upwardly.

In some non-limiting examples, a body can include an extension. A free end of the extension can extend past a center of mass of a urinal when the urinal does not include liquid positioned therein, a center of mass of the urinal when the urinal includes liquid positioned therein, or a centroid of the body of the urinal in a direction from a rear end to a front end of the body.

In some non-limiting examples, a body can include an extension and a ridge at a free end of the extension. The ridge can be configured to engage a supporting surface to mitigate tilting of a urinal.

In some non-limiting examples, a urinal can be formed of a polymer or a plastic.

In some non-limiting examples, a polymer or a plastic can be transparent or translucent.

In some non-limiting examples, a body of a urinal can define multiple walls. Each of the multiple walls of the urinal can have a thickness that can be less than 5.1 millimeters, or less than 1.3 millimeters.

In some non-limiting examples, a urinal that includes an internal volume can be configured to contain at least 1000 mL.

Some non-limiting examples of the disclosure provide a urinal system. The urinal system can include a first urinal including a first body, a first handle integrally formed with the first body, and a first recess directed into a bottom end of the first body. The urinal system can include a second urinal including a second body and a second handle integrally formed with the first body. The second handle of the second urinal can be inserted into the first recess of the first body of the first urinal. The first urinal can be positioned above the second urinal when the second handle of the second urinal is inserted into the first recess of the first urinal.

In some non-limiting examples, a second urinal can include a second recess directed into a bottom end of a second body. The urinal system can include a third urinal including a third body, and a third handle integrally formed with the third body. The third handle of the third urinal can be inserted into the second recess of the second urinal.

In some non-limiting examples, a first body of a first urinal can include a first extension. The first extension can be inserted into a first gap that can be between a first handle and a first body of the first urinal when a second handle is inserted into a first recess of the first urinal.

In some non-limiting examples, a first urinal can be in the same orientation as a second urinal when a second handle of the second urinal is inserted into a first recess of the first urinal.

Some non-limiting examples of the disclosure provide a method of packing multiple urinals in a container. The multiple urinals can include a first urinal and a second urinal. The method can include inserting a second handle of the second urinal into a first recess of the first urinal, the first recess being directed into a bottom end of a first body of the first urinal and inserting a first extension of the first urinal into a second gap of the second urinal. The second gap can be positioned between the second handle and a second body of the second urinal.

In some non-limiting examples, multiple urinals can include a third urinal. The method can include inserting a third handle of a third urinal into a second recess of a second urinal. The second recess can be directed into a bottom end of a second body of the second urinal.

In some non-limiting examples, a method can include placing multiple urinals into a container for shipping or storage of the multiple urinals.

In some non-limiting examples, each of the multiple urinals can be formed out of a plastic.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of non-limiting examples of the disclosure and are not intended to limit the scope of the disclosure or exclude alternative implementations.

DETAILED DESCRIPTION OF THE PRESENT DISCLOSURE

As described above, disposable urinals and particularly disposable urinals that are preformed (e.g., that have a single unitary body) can be difficult to pack, transport, and store. For example, typical disposable urinals can have a body and a handle that extends away from the body. While the handle can allow for more easier maneuverability of the disposable urinal, the handle can make packing the disposable urinals difficult and awkward within a container of multiple disposable urinals. For example, the handle of a disposable urinal can impede the smooth stacking of adjacent disposable urinals, which can result in significant packing inefficiencies. In other words, a first disposable urinal stacked on top of a second disposable urinal is blocked by the handle of the second disposable urinal from making flush contact with the second disposable urinal. In this way, there is significant dead space (e.g., open volume) within the container between rows of disposable urinals, leading to packing inefficiencies. These packing inefficiencies can make transporting disposable urinals more expensive (e.g., fuel, volume restrains within a vehicle, etc.), and can also undesirably require larger storage requirements at a health care facility.

Some non-limiting examples of the disclosure provide advantages to these issues (and others) by providing improved systems and methods for disposable urinals. For example, some non-limiting examples of the disclosure provide a urinal system including multiple urinals that are stackable and nestable (e.g., while stacked), which can considerably increase the packing efficiency of the multiple urinals. In other words, the spatial footprint of the multiple urinals when packed, stored, etc., can be considerably smaller than the spatial footprint of other typical urinals when packed, stored, etc. In this way, because the multiple urinals of the disclosure herein can be packed more efficiently, more urinals can be transported, stored, etc., in the same packing volume thereby significantly saving on transportation costs (e.g., fuel, labor, etc.).

Figure 1:
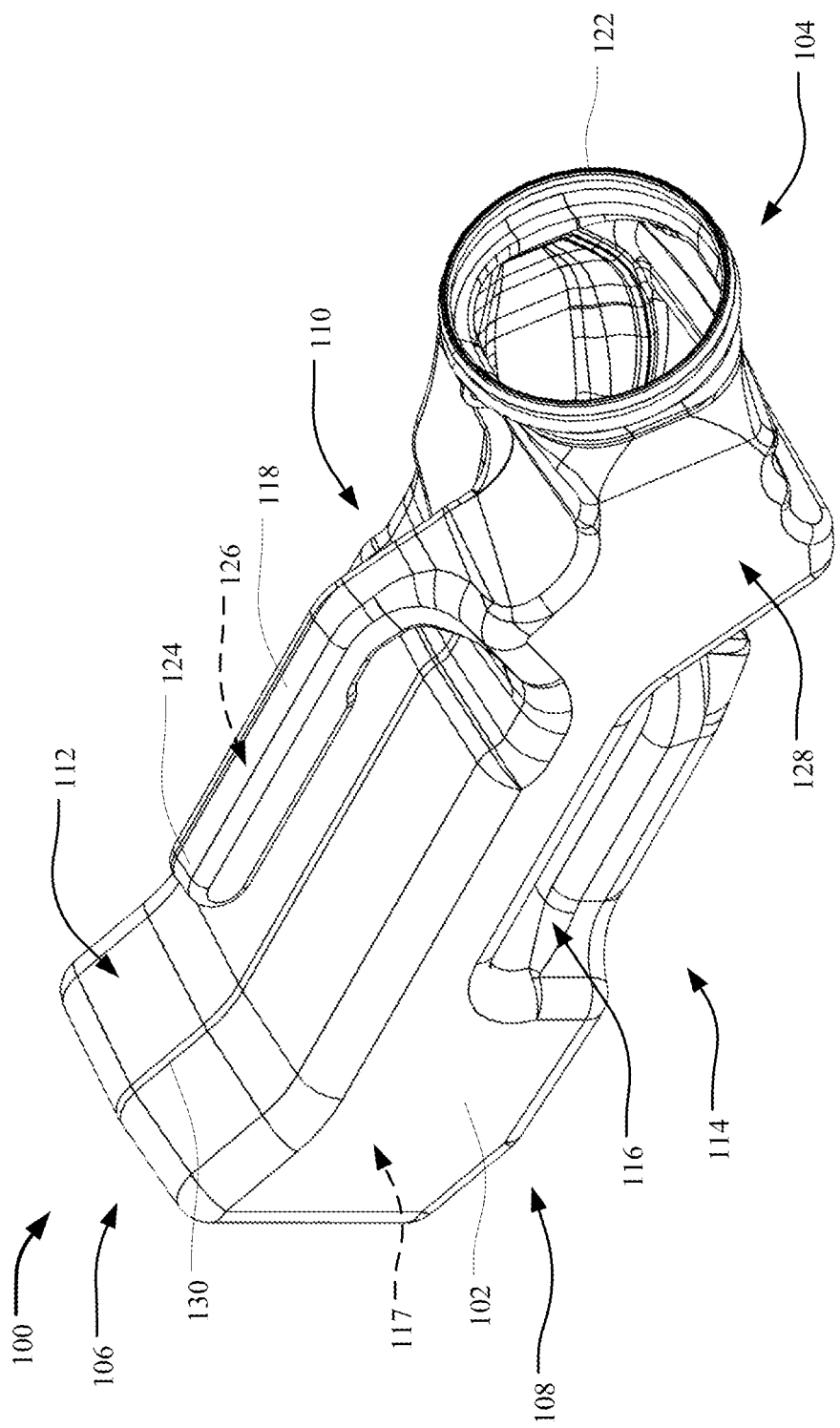
FIG. 1 shows a front isometric view of a urinal.

FIG. 1 shows a front isometric view of a urinal 100. The urinal 100 can include a body 102 that can define a front end 104, a rear end 106 opposite the front end 104, a first side 108 (e.g., a first lateral side), and a second side 110 (e.g., a second lateral side) opposite the first side 108, a top end 112, and a bottom end 114 opposite the top end 112. The body 102 of the urinal 100 can be hollow, and thus the body 102 can define an internal volume 117 that can receive (and contain) a liquid (e.g., urine) prior to disposal of the urinal 100 and the liquid therein. In some cases, the body 102 can include walls, each of which can define each end 104, 106, 112, 114, and each side 108, 110. For example, the body 102 can include a front wall that can define the front end 104, a rear wall that can define the rear end 106, a first side wall that can define the first side 108, a second side wall that can define the second side 110, a top wall that can define the top end 112, and a bottom wall that can define the bottom end 114. In some cases, each wall of the body 102 can have the same thickness or a different thickness. For example, each wall of the body 102 can have a thickness that is less than 5.1 millimeters, less than 1.3 millimeters, etc., with the thickness being greater than 0 millimeters.

In some cases, the urinal 100 can include a handle 118, a recess 116, and an opening 122. The handle 118 can be coupled to the body 102 of the urinal 100 and can extend away from the front end 104 and towards the rear end 106. For example, a free end 124 of the handle 118 can extend away from the front end 104 and towards the rear end 106. In some cases, the free end 124 of the handle 118 can be positioned closer to the rear end 106 than the front end 104. In some configurations, and similarly to the body 102, the handle 118 can be hollow, and thus the handle 118 can define an internal volume 126, which can be fluidly coupled to the internal volume 117 of the body 102. In other non-limiting examples, the internal volume 126 is not fluidly coupled to the internal volume 117 of the body 102. For example, the handle 118 can include a section that closes off the fluid connection between the internal volume 117 of body 102 and the internal volume 126 of the handle 118. As another example, the handle 118 can include an obstruction (e.g., a piece of material, such as the same material used to form the handle 118 or the body 102) that also blocks fluid communication. In some configurations, the handle 118 can be partially or entirely solid, which can provide more rigidity and support to the handle 118. In some non-limiting examples, while the handle 118 can be coupled to the body 102, the handle 118 can also be integrally formed with the body 102 (e.g., at the neck 128 of the body 102), or other portion of the urinal 100. In this way, a practitioner (e.g., a nurse, a nursing assistant, etc.) does not have to couple the handle 118 to the body 102 of the urinal 100, which can decrease the time, complexity, etc., needed to deliver the urinal 100 to a patient.

As shown in FIG. 1, the recess 116 can be directed into the body 102 and can extend from the front end 104 and towards the rear end 106. For example, the recess 116 can be directed into the bottom end 114 of the body 102 and can extend towards the rear end 106 of the body 102 (e.g., stopping before extending entirely through the rear end 106 of the body 102). The recess 116 can have a shape that corresponds to a shape of a handle of a urinal. For example, the recess 116 can have a shape that corresponds to the shape of the handle 118. In this way, the recess 116 can accommodate a handle of a second urinal to facilitate more efficient stacking of urinals. In other words, the recess 116 can receive a handle of a second urinal, so that the handle of the second urinal can nest within the recess 116. In some non-limiting examples, the opening 122 can be fluidly coupled to the internal volume 117 of the body 102 and can be positioned at the front end 104 of the body 102. For example, the body 102 of the urinal 100 can include a neck 128, which can define the front end of the body 102, and the opening 122 can be positioned at a first portion of the neck 128 that has a greater cross-section than a second portion of the neck 128. For example, the neck 128 can decrease in cross section in a direction from the rear end 106 and towards the front end 104 along a longitudinal axis of the body 102 until the neck 128 reaches a local minima in cross-section. At this point, the neck 128 can increase in cross-section until the neck 128 ends at the opening 122. The opening 122 can provide access to the internal volume 117 of the body 102 to, for example, receive and contain a liquid (e.g., urine) for collection and subsequent disposal.

In some non-limiting examples, the urinal 100 can be formed out of different materials. For example, the urinal 100 can be formed out of a polymer (e.g., a plastic), a metal, etc. As a more specific example, the urinal 100 can be formed out of polyurethane, polypropylene, polyethylene, polyethylene, PET polyester, polyvinyl chloride, etc. In some cases, the urinal 100 can be formed out of a thermopolymer (e.g., a thermoplastic), which can include a polymer that can be melted, ground, and re-melted. For example, the urinal 100 can be formed by blow molding (e.g., of a polymer, plastic, etc.). In this case, the urinal 100 can include a seam 130 (e.g., which can include a ridge, such as a small ridge) that can extend along a portion or the entire body 102. In addition, the seam 130 can extend along a portion of the handle 118, a portion of the body 102 at the opening 122, a portion of the body 102 at the recess 116, a portion of the extension 132, a portion of the body 102 outside of the recess 116, a portion of the body 102 not at the opening 122, etc. In some cases, the seam 130 (and ridge) can be indicative of the interface between respective ends of the two halves of the mold used to form the urinal 100 (e.g., by blow molding).

Figure 2:
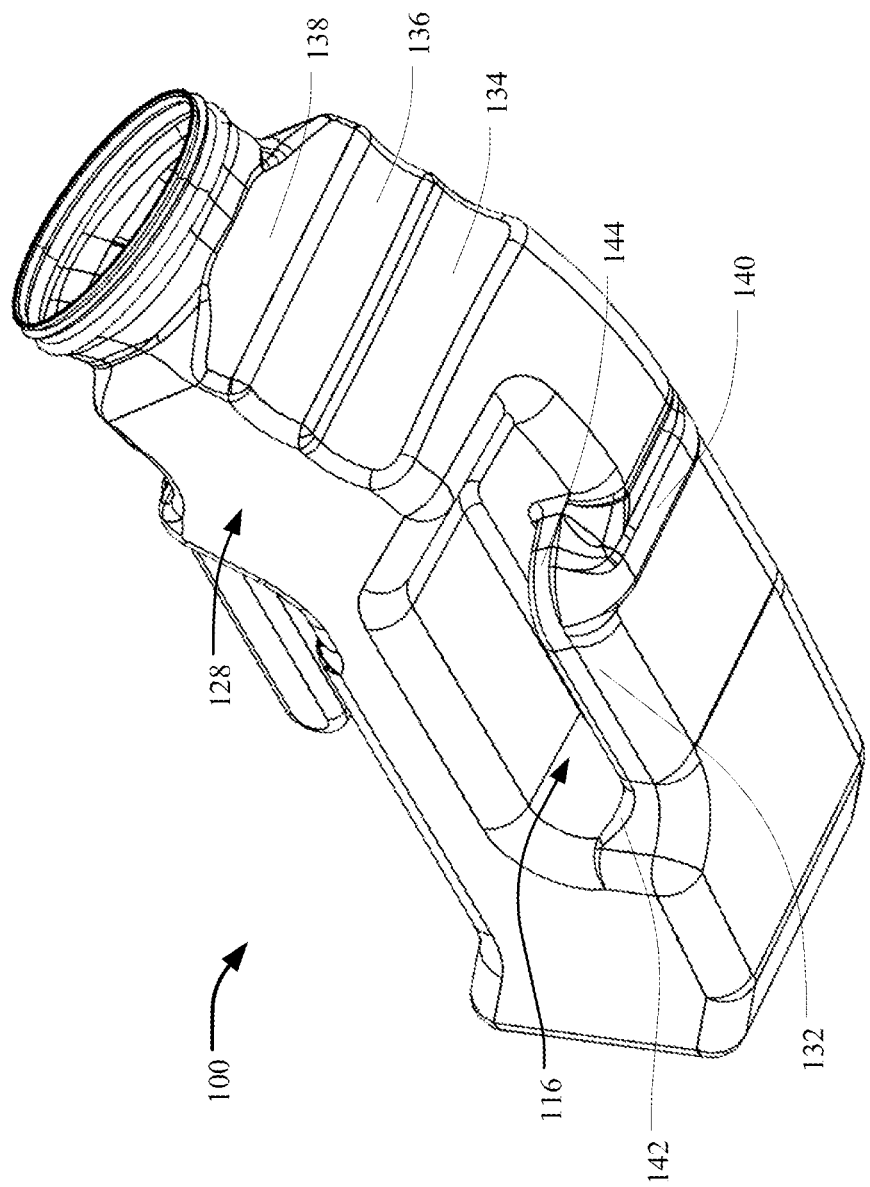
FIG. 2 shows a bottom isometric view of the urinal of FIG. 1.

FIG. 2 shows a bottom isometric view of the urinal 100. As shown in FIG. 2, the urinal 100 can include an extension 132, recesses 134, 136, 138, and a ridge 140. For example, the body 102 can include the extension 132, which can extend away from the rear end 106 and towards the front end 104. In some cases, the extension 132 can extend away from the second side 110 and towards the first side 108. Regardless, the extension 132 can at least partially define the recess 116. For example, the extension 132 can define a wall that can block movement of the handle of the second urinal when the handle of the second urinal is positioned within the recess 116. In some cases, the extension 132 can have curved regions 142, 144, each of which can facilitate easier removal or insertion of the handle of the second urinal into the recess 116. For example, the curved region 142 can be concave, while the curved region 144 can be convex, and the curved region 142 can be positioned further towards the rear end 106 than the curved region 144. The decrease in material at the curved regions 142, 144 can provide smoother removal or insertion of the handle of the second urinal into the recess 116 at least because the extra material, which would have otherwise blocked insertion (or removal) of the handle, has been removed. In addition, without the extra material, the handle of the second urinal can be rotated to a first orientation, can be inserted into the recess 116 while rotated in the first orientation, and can be rotated away from the first orientation while positioned within the recess 116 until the handle of the second urinal is locked in place.

As shown in FIG. 2, the urinal 100 can include the recesses 134, 136, 138, each of which can be directed into the body 102 of the urinal 100 (e.g., directed into the front end 104 of the body 102 of the urinal 100, directed into the bottom end 114 of the body 102 of the urinal 100, etc.). In particular, each recess 134, 136, 138 can be directed into the neck 128 of the body 102 of the urinal 100. In some non-limiting examples, the recess 136 can be positioned between the recesses 134, 138. For example, the recess 138 can be positioned above the recesses 134, 136, the recess 136 can be positioned above the recess 134 and below the recess 138, and the recess 134 can be positioned below the recesses 136, 138. In some non-limiting examples, while the recesses 134, 136, 138 are illustrated as extending across the entire bottom end 114 of the body 102 (e.g., extending past the handle 118, extending past the opening 122, etc.), the recesses 134, 136, 138 can extend partially across the bottom end 114 of the body 102. In some non-limiting examples, each recess 134, 136, 138 can be curved, which can facilitate better nesting of particular components of the second urinal (and a third urinal) within the urinal 100. For example, as described in more detail below, the recess 134 can receive a loop of the second urinal that is configured to receive a tether, the recess 136 can receive a portion of the body of the second urinal at the opening of the second urinal (e.g., a mouth of the second urinal, and in particular an upper end of the body of the second urinal can contact the body 102 at the recess 136), and the recess 138 can receive a portion of a body of a third urinal at the opening of the third urinal (e.g., a mouth of the third urinal, and in particular a lower end of the body of the third urinal can contact the body 102 at the recess 138). Thus, each recess 134, 136, 138 can accommodate different portions of different urinals to more efficiently stack, pack, etc., multiple urinals (e.g., within a container).

In some non-limiting examples, the urinal 100 can include the ridge 140, which can be configured to stabilize the urinal 100 (e.g., when the urinal 100 is supported by a supporting surface). For example, the body 102 of the urinal 100 can include the ridge 140, and the ridge 140 can be positioned at and can extend away from the bottom end 114 of the body 102 of the urinal 100. In some cases, and as illustrated, the ridge 140 can extend across the entire bottom end 114 of the body 102 of the urinal 100. However, in other configurations, the ridge 140 can extend partially across bottom end 114 of the body 102 of the urinal 100. In some non-limiting examples, the ridge 140 can be positioned at the recess 116 (e.g., so that the ridge 140 extends partially across the recess 116). For example, the ridge 140 can extend across a portion (or the entire) extension 132. In some configurations, the ridge 140 can extend across a portion of (or the entire) handle 118.

Figure 3:
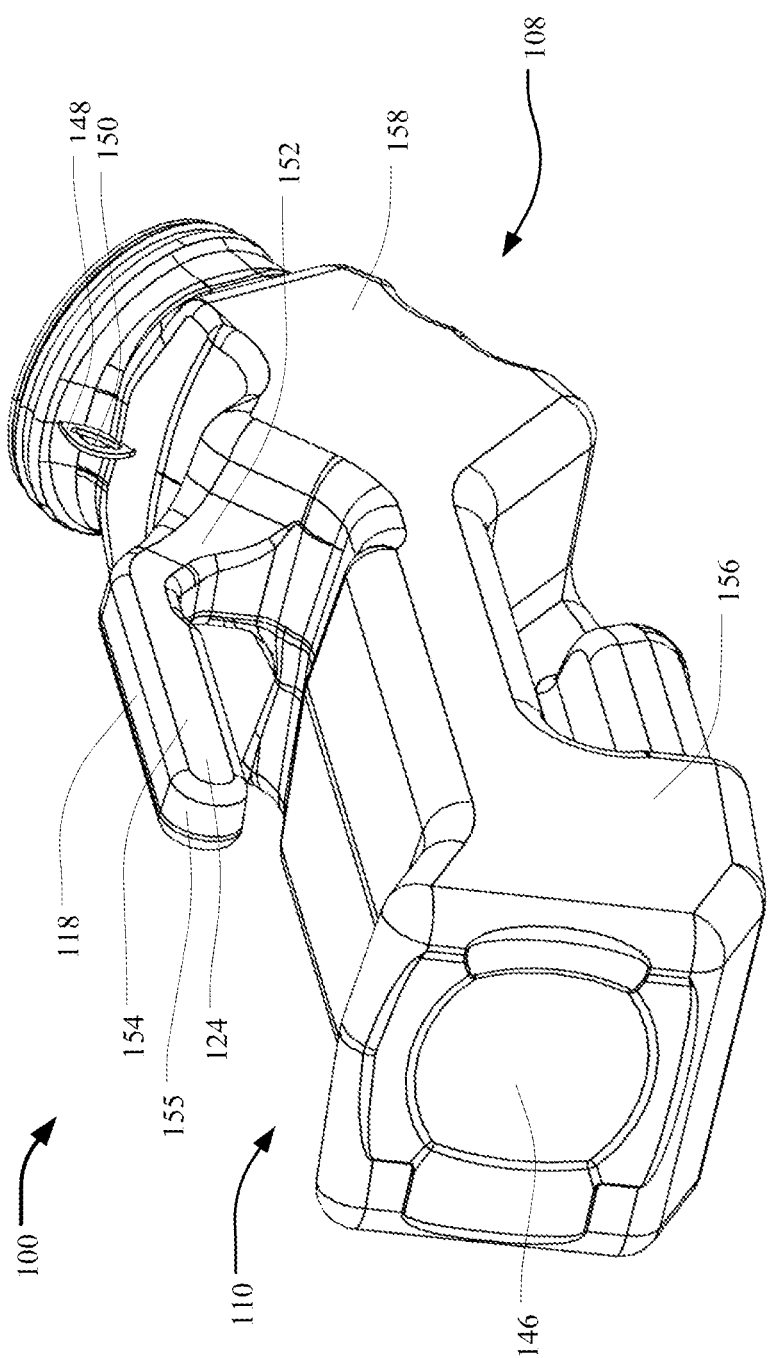
FIG. 3 shows a rear isometric view of the urinal of FIG. 1.

FIG. 3 shows a rear isometric view of the urinal 100. As shown in FIG. 3, the urinal 100 can include a recess 146, and a loop 148. For example, the recess 146 can be directed into the rear end 106 of the body 102 of the urinal 100, which can provide stability for the urinal 100, when, for example, the urinal 100 is being supported on the rear end 106 of the body 102 (e.g., when the rear end 106 of the urinal 100 is contacting a supporting surface, which can include a longitudinal axis of the body 102 being substantially parallel with a gravity vector). As shown in FIG. 3, the urinal 100 can include a loop 148 that can be configured to receive a tether (not shown) that is coupled to a cap (not shown). The loop 148 can be integrally formed with the body 102 of the urinal 100 and can be positioned at the top end 112 of the body 102 and closer to the front end 104 than the rear end 106 of the body 102. For example, the loop 148 can be positioned proximal to the opening 122 of the urinal 100. In some embodiments, the loop 148 can be positioned at the neck 128 of the body 102. In some cases, the loop 148 can define a hole 150, which can receive the tether. In this way, the cap that is coupled to the tether is secured to the urinal 100 to avoid losing the cap (e.g., after using the urinal 100).

In some non-limiting examples, the handle 118 can include a base 152, and an arm 154 extending away from the base 152 that can define the free end 124 of the handle 118. As shown in FIG. 3, the base 152 is integrally formed with the body 102 of the urinal 100 (e.g., at the neck 128) and extends away from the front end 104 of the body 102 towards the rear end 106 of the body 102. For example, the base 152 can be angled away from the front end 104 of the body 102 such that an upper end of the base 152 is positioned further away from the front end 104 than a lower end of the base 152. In some non-limiting examples, and as illustrated, the base 152 can decrease in cross-section along the length of the base 152 (e.g., along a portion or the entire base 152). As shown in FIG. 3, the arm 154 can be integrally formed with the base 152 and can extend away from the front end 104 and towards the rear end 106 of the body 102. In some cases, the arm 154 can extend past a centroid of the body 102, a center of mass of the body 102 (e.g., when the body 102 contains a liquid), etc. In some cases, the arm 154 can extend in a substantially straight direction (e.g., the arm 154 can be substantially linear), which can include the arm 154 being substantially parallel to a longitudinal axis of the body 102 of the urinal 100. In some non-limiting examples, the free end 124 of the handle 118 (e.g., the arm 154 of the handle 118) can be curved. For example, the free end 124 of the handle 118 can define a curved region 155, which can be convex. In this way, the curved region 155 can avoid edges, pointed regions, etc., that could be uncomfortable for a user when grasping the handle 118.

In some non-limiting examples, and as described above, the body 102 can include one or more walls. For example, the body 102 can include a side wall 156 that can define the first side 108 of the body 102. In some cases, a portion (or the entire) side wall 156 can be substantially flat, which can, as described in more detail below, provide a flat surface for compression of a raised portion of a urinal (e.g., the second urinal). For example, the side wall 156 can define a substantially flat portion 158, which can extend across at least 50 percent of the area of the side wall 156.

Figure 4:
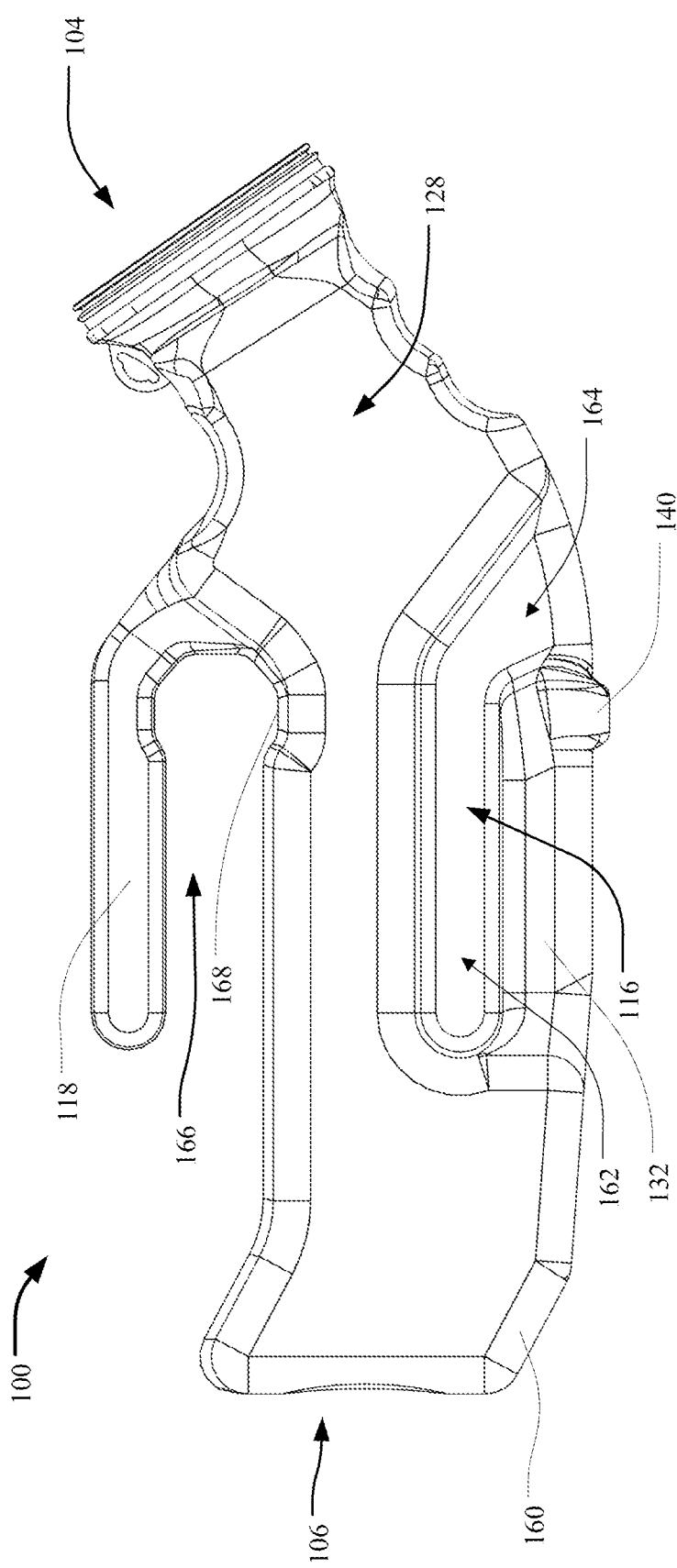
FIG. 4 shows a side view of the urinal of FIG. 1.
Figure 14:
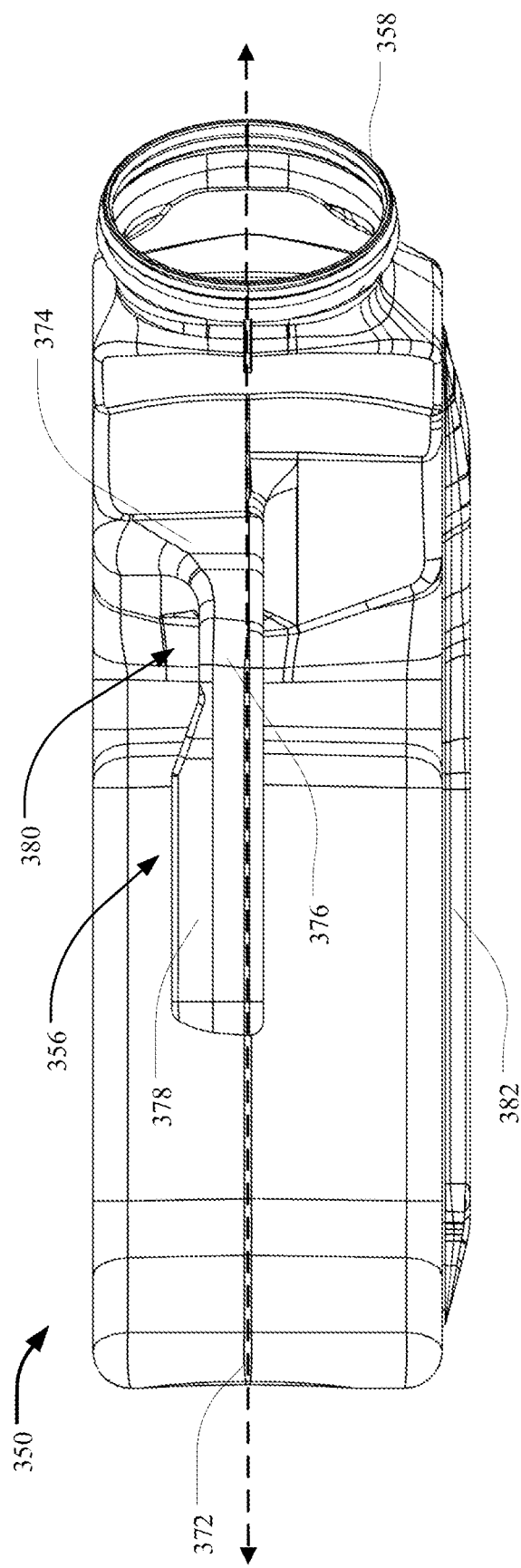
FIG. 14 shows a top view of the urinal of FIG. 12.

FIG. 4 shows a side view of the urinal 100. As shown in FIG. 14, opposing ends of the body 102 can be angled, curved, or both, upwardly. For example, the rear end 106 can extend upwardly (e.g., relative to a longitudinal axis of the body 102), and the front end 104 can extend upwardly. For example, a portion 160 of the body 102 at the rear end 106 can be angled upwardly at an angle relative to the longitudinal axis of the body 102. Correspondingly, the neck 128 of the body 102 can be curved upwardly (or angled upwardly), which can be relative to the longitudinal axis of the body 102. This curved shape of the body 102 can increase the stability of the urinal 100 (e.g., to prevent the urinal 100 from tilting and thus spilling when the urinal 100 is in the horizontal orientation such as the view in FIG. 4). In some non-limiting examples, the recess 116 can accommodate different portions of a handle of the second urinal, which can be similar to the structure of the handle 118). For example, the recess 116 can include portions 162, 164. The portion 162 can be positioned closer to the rear end 106 of the body 102 than the portion 164. Correspondingly, the portion 164 can be positioned closer to the front end 104 of the body 102 than the portion 162. In some cases, the portion 164 can be directed into the bottom end 114 of the body 102 and can extend at an angle towards the rear end 106 of the body 102. In some cases, the angle of the portion 164 can be substantially the same as the angle of the base 152 of the handle 118, and the length of the portion 164 can be substantially the same as the length of the base 152. In this way, the portion 164 can receive a corresponding base of the handle of a second urinal. Correspondingly, the portion 162 can extend towards the rear end 106 of the body 102 away from the portion 164 (e.g., an end of the portion 164 that is positioned away from the bottom end 114 of the body 102). In some cases, the portion 162 of the recess 116 can be substantially straight, and the length of the portion 162 can be substantially the same the length of the handle 118. In this way, the portion 162 of the recess 116 can receive a corresponding arm of the handle of the second urinal. In some non-limiting examples, an end of the portion 162 can be concave, which can allow for a better engagement with a curved region 155 of the handle of the second urinal (e.g., similarly to the curved region 155 of the free end 124 of the handle 118).

In some non-limiting examples, the urinal 100 can include a gap 166 positioned between the handle 118 and the body 102. In some cases, the gap 166 can include a concave region 168, which can be positioned at an end of the gap 166 that is closer to the body 102. In some cases, the concave region 168 (e.g., which can be directed into the body 102) can receive a ridge of the third urinal (e.g., similar to the ridge 140 of the urinal 100). In this way, the gap 166 can accommodate a ridge of the third urinal to more efficiently stack the urinals. In some non-limiting examples, the concave region 168 can correspond in shape to the ridge 140.

In some non-limiting examples, the extension 132 can be configured to mitigate tilting of the urinal 100, which could cause the urinal 100 to spill liquid (e.g., out of the opening 122). For example, the extension 132 can extend past a center of mass of the urinal 100 when the urinal does not include liquid (e.g., urine) positioned within the internal volume 117 of the body 102, a center of mass of the urinal 100 when the urinal 100 includes liquid positioned therein (e.g., at least 100 mL, at least 200 mL, at least 300 mL, at least 400 mL, at least 500 mL, at least 600 mL, at least 700 mL, at least 800 mL, at least 900 mL, at least 1000 mL, etc.), a centroid of the body 102 of the urinal 100 in a direction from the rear end to the front end of the body. In other words, a free end of the extension 132 (e.g., including the ridge 140) can be positioned closer to the front end 104 of the body 102 than the center of mass of the urinal 100 when the urinal 100 does not include liquid, the center of mass of the urinal 100 when the urinal 100 includes liquid, and the centroid of the body 102 of the urinal 100. In some non-limiting examples, the ridge 140 can be configured to mitigate tilting of the urinal 100. For example, the ridge 140 can engage a supporting surface (e.g., a table, the floor, etc.), which can prevent rocking, tilting, etc., of the urinal 100, especially when the supporting surface is angled (e.g., angled downwardly).

As shown in FIG. 3, the arm 154 can be integrally formed with the base 152 and can extend away from the front end 104 and towards the rear end 106 of the body 102. In some cases, the arm 154 can extend past a centroid of the body 102, a center of mass of the body 102 (e.g., when the body 102 contains a liquid), etc. In some cases, the arm 154 can extend in a substantially straight direction (e.g., the arm 154 can be substantially linear), which can include the arm 154 being substantially parallel to a longitudinal axis of the body 102 of the urinal 100. In some non-limiting examples, the free end 124 of the handle 118 (e.g., the arm 154 of the handle 118) can be curved. For example, the free end 124 of the handle 118 can define a curved region 155, which can be convex. In this way, the curved region 155 can avoid edges, pointed regions, etc., that could be uncomfortable for a user when grasping the handle 118.

Figure 5:
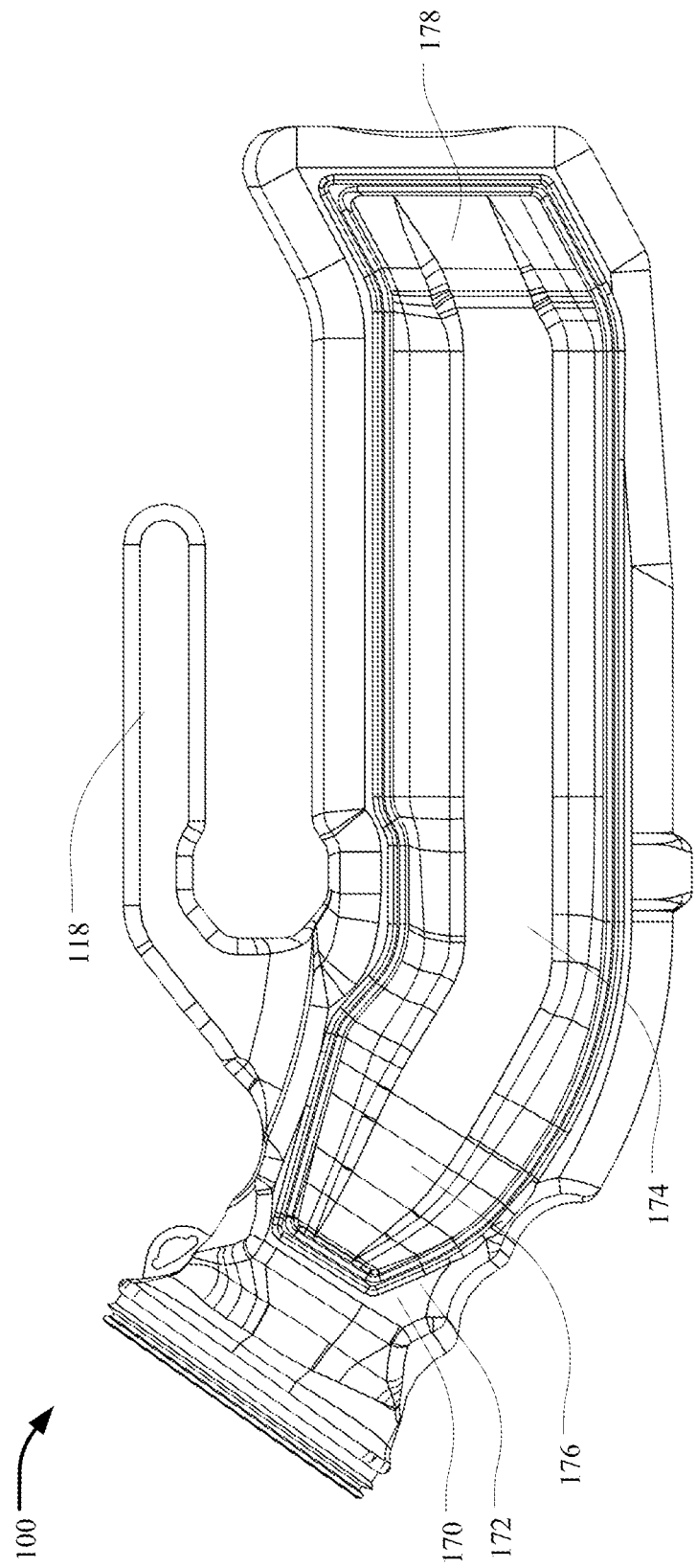
FIG. 5 shows another side view of the urinal of FIG. 1.

FIG. 5 shows a side view of the urinal 100, which is the opposing side view as the side view in FIG. 4. As shown in FIG. 5, the body 102 of the urinal 100 can include a side wall 170 that can define the second side 110 of the body 102. In some cases, the side wall 170 can include a substantially flat portion 172, and a raised portion 174 (e.g., that extends past the substantially flat portion 172). As shown in FIG. 5, the raised portion 174 can be larger than the substantially flat portion 172 (e.g., the raised portion 174 can span an area that is larger than the substantially flat portion 172), and a portion of or the entire substantially flat portion 172 can surround the raised portion 172. In some cases, the raised portion 172 can span substantially the entire side wall 170 (e.g., with the remaining portion being the substantially flat portion 172). In some configurations, the raised portion 172 can span at least 50% of the entire area of the side wall 170. As shown in FIG. 5, the raised portion 172 can contour the shape of the body 102 (e.g., along a longitudinal axis of the body 102). For example, ends 176, 178 of the raised portion 172 can be curved or angled upwardly (e.g., along a longitudinal axis of the body 102). For example, the end 176 of the raised portion 172 can be curved upwardly along the neck 128 of the body 102 (e.g., relative to the longitudinal axis of the body 102), which is also angled upwardly. Correspondingly, the end 178 of the raised portion 172 can be angled upwardly (e.g., relative to the longitudinal axis of the body 102) along the portion 160 of the body 102 at the rear end 106 that is angled upwardly. In some cases, the cross-section of the raised portion 174 can decrease along the length of the body 102 in a direction towards the front end 104 of the body 102. For example, the end 176 of the raised portion 174 can have a cross-section that is smaller than a cross-section of the raised portion 174 at a central portion of the raised portion 174.

In some non-limiting examples, the raised portion 174 is configured to be compressed into a compressed state (e.g., during shipment, transportation, etc.) and is configured to expand from the compressed state to an expanded state to define the raised portion 174. In this way, when expanded (e.g., not compressed) the raised portion 174 can advantageously provide an increased internal volume 117 of the body 102 of the urinal 100 (e.g., so that the urinal can hold more liquid). Corresponding, the raised portion 174 can be compressed (e.g., against a substantially flat portion of the second urinal similar to the substantially flat portion 158 of the urinal 100), which can compress the raised portion 174 thereby decreasing the internal volume 117 of the body 102 of the urinal 100 (e.g., during transport). In this way, the spring-like ability of the raised portion 174 to be compressed and subsequently expanded can not only allow for more efficient packing of the urinals (e.g., because the width of the urinal can decrease by compressing the raised portion 174) but can also increase the internal volume 117 (e.g., to hold more liquid, such as urine) when the urinals are unpacked and expanded. In some configurations, the raised portion 174 (and other raised portions of other urinals) when compressed into a container during shipment, transport, etc., can improve the stability of the urinals. In other words, the urinals, via the spring-like raised portions, are forced against walls of the container, which can minimize shifting of the urinals during transport. In some non-limiting examples, when the raised portion 174 is compressed, the raised portion 174 can be substantially flat and can align with the substantially flat portion 172 of the side wall 170.

Figure 6:
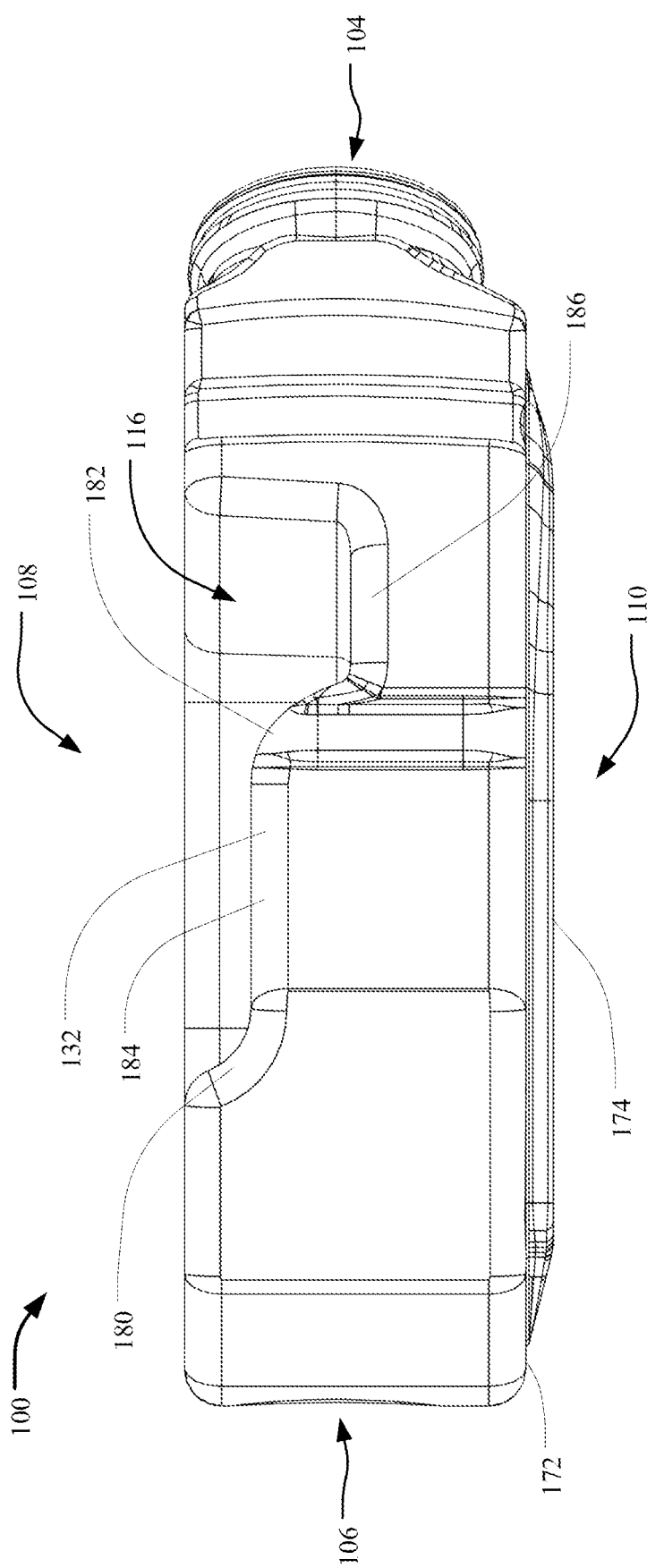
FIG. 6 shows a bottom view of the urinal of FIG. 1.

FIG. 6 shows a bottom view of the urinal 100. As shown in FIG. 6, the extension 132 can have a non-uniform cross section (e.g., along the longitudinal axis of the body 102). For example, the extension 132 can decrease in a direction from the rear end 106 to the front end 104 of the body 102. As a more specific example, the extension 132 can include ledges 180, 182, that are situated between substantially linear portions 184, 186 of the extension 132. For example, the substantially linear portion 184 can be positioned between the ledges 180, 182, while the substantially linear portion 186 can be positioned closer to the front end 104 of the body 102 than the ledges 180, 182, and the substantially linear portion 184. In some cases, the substantially linear portion 184 can be longer than the substantially linear portion 186. As shown in FIG. 6, the cross-section of the extension 132 can decrease along the ledge 180 (e.g., which can be concave), can be substantially uniform along the substantially linear portion 184, decreases along the ledge 182 (e.g., which can be convex), and can be substantially uniform along the substantially linear portion 186.

Figure 7:
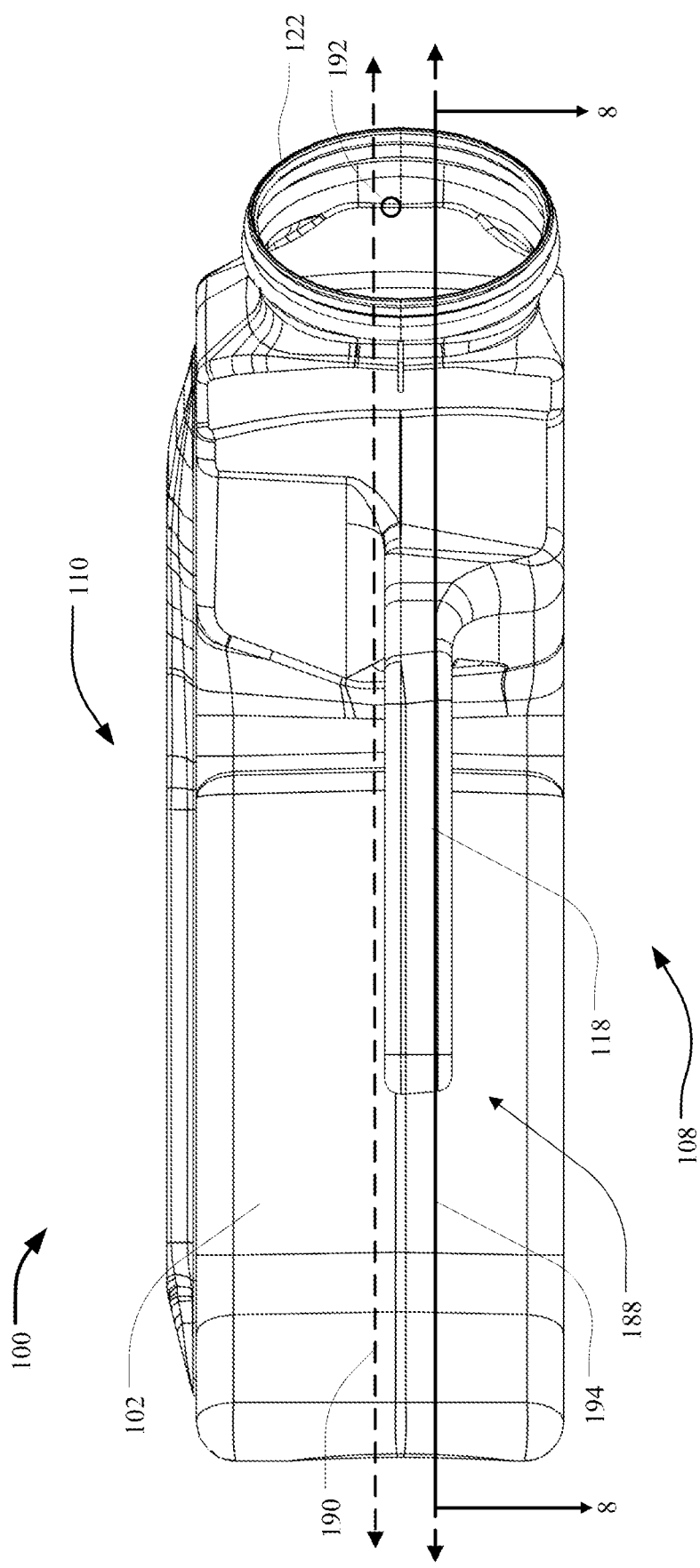
FIG. 7 shows a top view of the urinal of FIG. 1.

FIG. 7 shows a top view of the urinal 100. As shown in FIG. 7, the body 102 can include a portion 188 (e.g., a rear portion) that can be bisected by a longitudinal axis 190 of the body 102 (e.g., into two equal halves of the portion 188 of the body 102). In some cases, this longitudinal axis 190 (e.g., which can extend past the front end 104 and rear end 106 of the body 102) can define the first side 108 of the body 102 and the second side 110 of the body 102. In some non-limiting examples, some components including portions thereof of the urinal 100 can be positioned on only the first side 108. For example, a portion of (or the entire) handle 118, a portion of (or the entire) recess 116, a portion of (or the entire) extension 132, a center 192 of the opening 122 (e.g., the center 192 being the centroid of the opening 122) can be positioned on only the first side 108 of the body 102 (e.g., not positioned on the second side 110 of the body 102). In some cases, the positioning of these components can be desirable over alternative configurations. For example, the recess 116 being positioned on only one side of the body 102 not only accommodates the handle of a second urinal (similar to the urinal 100) for easy insertion and removal, but also minimizes the extent of the recess 116 into the body 102 (e.g., the size of the recess 116), which decreases the internal volume 117 of the body 102. In other words, larger recesses can undesirably decrease the size of the internal volume 117. For example, if the handle 118 were centrally located on the body 102, the recess would have to extend through the entire body 102 from one side to the other (e.g., because having only a centrally located recess in the body 102 would not allow a handle of a second urinal to fit into the centrally located recess). Thus, the recess 116, while accommodating the centrally located handle, would significantly decrease the internal volume 117 of the urinal 100.

In some non-limiting examples, the positioning of these components on only one side of the body 102 can be desirable over alternative configurations. For example, during blow molding processes, having features that are aligned (e.g., that are symmetrical about an axis) can be desirable at least because molding can be less complicated, the resulting part can be more stable (e.g., because the ridge that is indicative of the interface between the two halves of the mold extends uniformly along the part), etc. Thus, in some cases, a longitudinal axis 194 that is offset from the longitudinal axis 190 (e.g., and can be parallel to the longitudinal axis 190) can extend through the handle 118, extend through the recess 116, extend through the extension 132, extend through the ridge 140, and extend through the opening 122.

Figure 8:
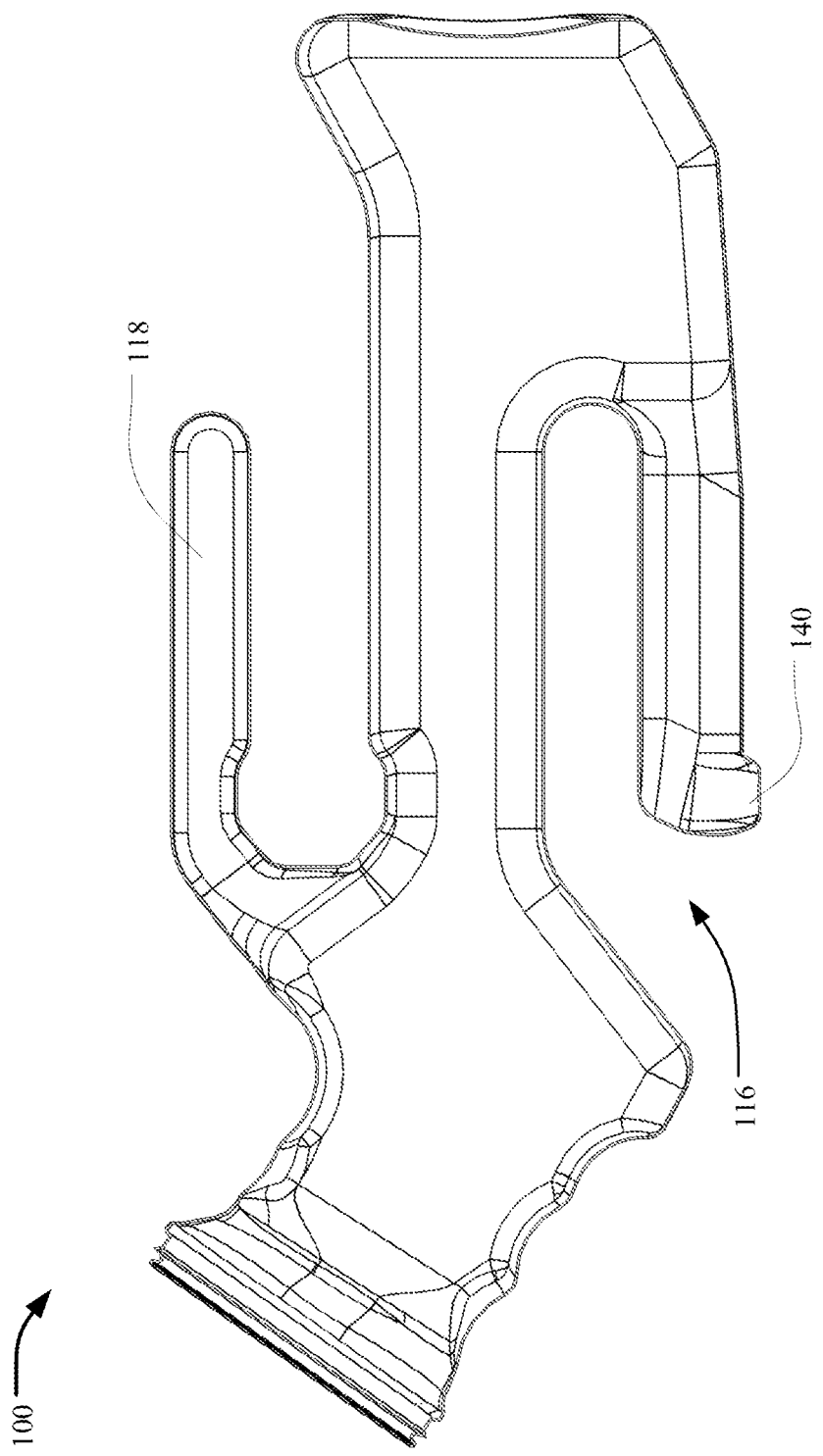
FIG. 8 shows a cross-sectional view of the urinal of FIG. 1, taken along line 8-8 of FIG. 7.

FIG. 8 shows a cross-sectional view of the urinal 100 taken along line 8-8 of FIG. 7. In particular, FIG. 8 shows a plane that defines the cross-sectional view of the urinal 100, which can be aligned with the longitudinal axis 194. As shown in FIG. 8, the handle 118, the recess 116, the extension 132, and the ridge 140 can be coplanar. For example, at least a portion of the handle 118, at least a portion of the recess 116, at least a portion of the extension 132, and at least a portion of the ridge 140 can be coplanar (e.g., residing within the same plane that can intersect with the longitudinal axis 194).

Figure 9:
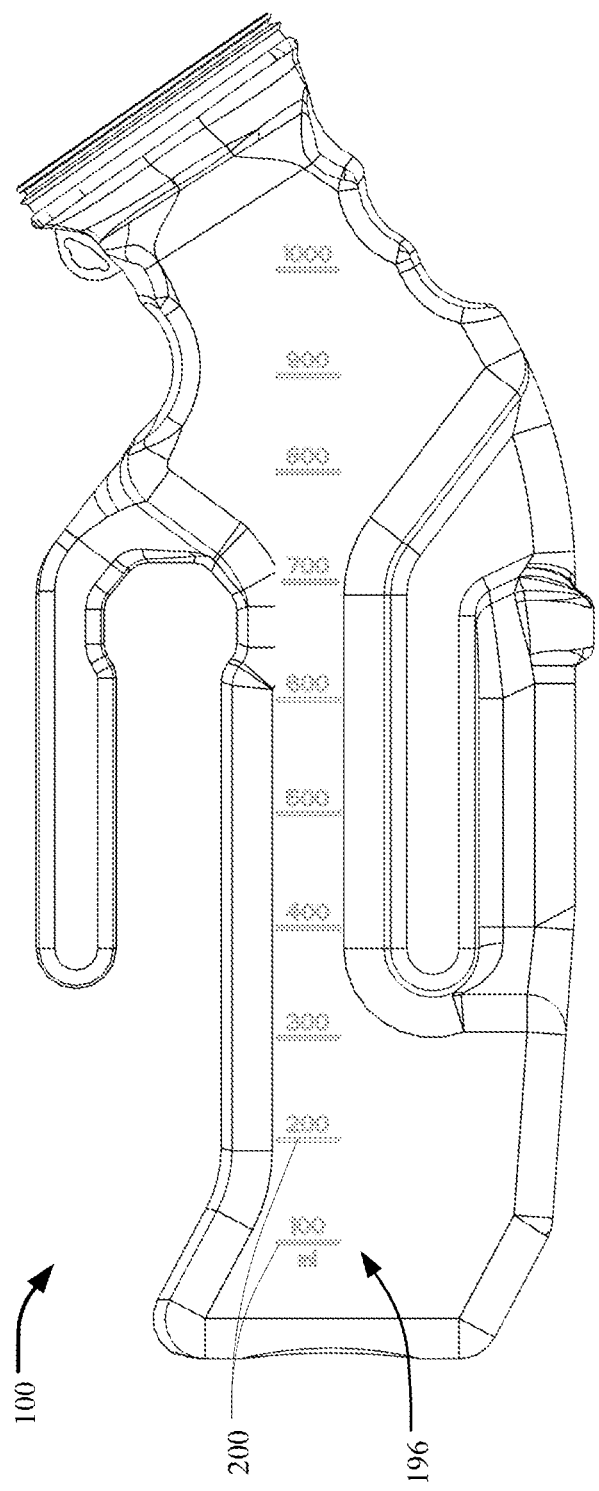
FIG. 9 shows another side view of the urinal of FIG. 1.
Figure 10:
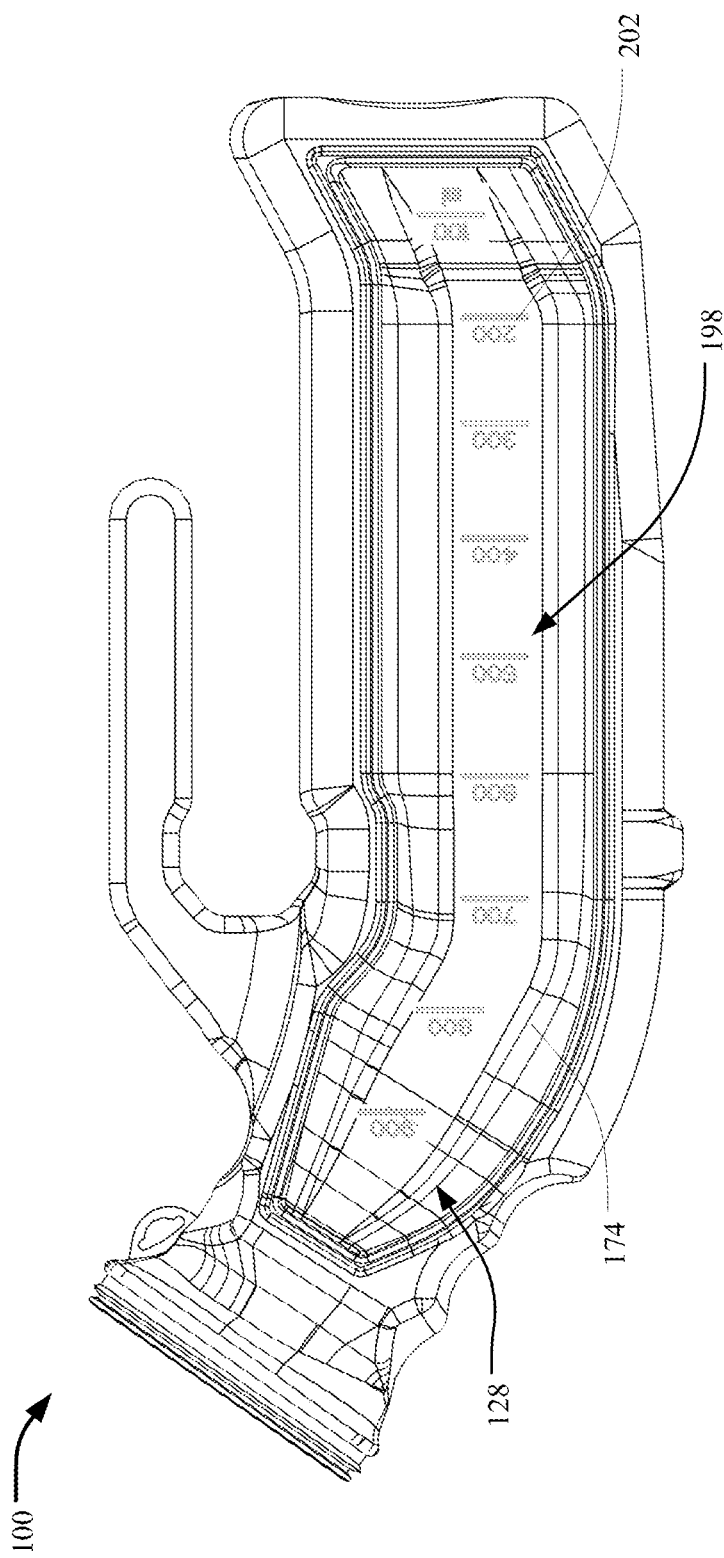
FIG. 10 shows a side view of the urinal of FIG. 1.

FIG. 9 shows a side view of the urinal 100 (e.g., which can be similar to the view of FIG. 4), while FIG. 10 shows a different side view of the urinal 100 (e.g., which can be similar to the side view of FIG. 5). As shown in FIGS. 9 and 10, the urinal 100 can include one or more indicia that can indicate the amount of liquid positioned within the internal volume 117 of the body 102 of the urinal 100. For example, each side of the urinal 100 can include respective indica. In particular, the urinal 100 can include an indicia 196 positioned on the first side 108 of the body 102 of the urinal 100, and an indicia 198 positioned on the second side 110 of the body 102 of the urinal 100. Each indicia 196, 198 can include one or more markings (e.g., a line) and a corresponding numeral that identifies the particular volume value when liquid is filled at the particular marking. For example, the indicia 196 can include a plurality of markings 200 each having a line and a numeral that indicates the particular volume level of liquid contained by the urinal 100. Correspondingly, the indicia 198 can also include a plurality of markings 202 each having a line and a numeral that indicates the particular volume level of liquid contained by the urinal 100. As shown in FIG. 10, the indicia 198 including the plurality of markings 202 can be positioned on the raised portion 174 of the urinal 100.

In some non-limiting examples, each of the plurality of markings 200, 202 can contour the shape of the body 102 of the urinal 100 along the particular side of the urinal 100. For example, as shown in FIG. 10, some of the markings 202 are positioned higher than some of the other markings 202. In particular, a first set of the markings 202 can be centrally located on the body 102, a second set of markings 202 can be positioned on the neck 128 of the body 102 above the first set of markings 202, and a third set of markings 202 can be positioned proximal the rear end 106 of the body 102 and above the first set of markings 202 (e.g., with each set of markings being at least one marking). In other configurations, the plurality of markings 200, 202 can extend in different ways along the body 102. For example, as shown in FIG. 9, the plurality of markings 200 can extend in a line along the body 102 (e.g., with an axis, line, etc., intersecting each marking 200). In some non-limiting examples, each indicia 196, 198 can be coupled to the body 102 at the respective side of the body 102. For example, in this case, each indicia 196, 198 can be an adhesive label that can be coupled to the body 102 (e.g., after the body 102 is formed). In other cases, each indicia 196, 198 can be integrally formed with the body 102. In this case, each indicia 196, 198 can be raised or recessed regions of the body 102.

In some non-limiting examples, the body 102 can be formed out of a transparent or a translucent material (e.g., plastic). In this way, the liquid including the liquid level within the body 102 can be visible outside of the body 102. Thus, a user can, using the viewable liquid level and an indicia, determine when the liquid has reached a particular volume including when the urinal 100 is full of liquid.

In some non-limiting examples, some or all of the components, features, etc., of the urinal 100 can be hollow (as appropriate) to advantageously increase the size of the internal volume 117 of the body 102 of the urinal 100. For example, the extension 132 can be hollow (e.g., the internal volume 117 of the body 102 can extend into the extension 132) to define an extension internal volume that can contain, hold, etc., liquid. As another example, the ridge 140, the raised portion 174, the handle 118, etc., can each be hollow and thus each of these can contain a liquid.

In some non-limiting examples, some or all the components of the urinal 100 can be integrally formed with each other, as appropriate. In other words, the some or all the components of the urinal 100 can form a single unitary component (e.g., the body 102), as appropriate. In this way, the body 102 of the urinal 100 can include some or all of the components of the urinal 100, such as, for example, the handle 118, the extension 132, the ridge 140, etc. In some non-limiting examples, having a single unitary body of the urinal 100 (e.g., the body 102) can be desirable for practitioners over other configurations. For example, a single unitary body requires little to no assembly of the urinal 100, and thus the practitioner can simply grasp the body 102 of the urinal 100 (e.g., after disengaging the urinal 100 from another urinal nested thereto) to deliver the urinal 100 to the patient, rather than assembling, fastening, etc., multiple pieces of a urinal together prior to delivery to the patient. Thus, disposable urinals with a single unitary body can be considerably more user friendly (e.g., for nurses, nursing assistants, etc.).

In some non-limiting examples, while the urinal 100 is illustrated as being a male urinal, in other configurations, the urinal 100 can be implemented as a female urinal. In this case, for example, a cup can be coupled to the body 102 of the urinal 100 (e.g., at the opening 122). In particular, the cup can be threadingly engaged with the body 102 of the urinal at the opening 122 to fasten the cup to the body 102 of the urinal. In other cases, the cup can be integrally formed with the body 102.

In some non-limiting examples, the urinal 100 is configured to contain at least 1000 mL. For example, the internal volume 117 of the body 102 of the urinal 100 can be at least 1000 mL. In some non-limiting examples, while not shown, the urinal 100 can include a cap that can be coupled to the loop 148 and can be coupled to the body 102 at the opening 122 (e.g., by threadingly engaging the cap with the body 102 at the opening 122) to seal the internal volume 117 and the liquid positioned therein from the ambient environment.

Figure 11:
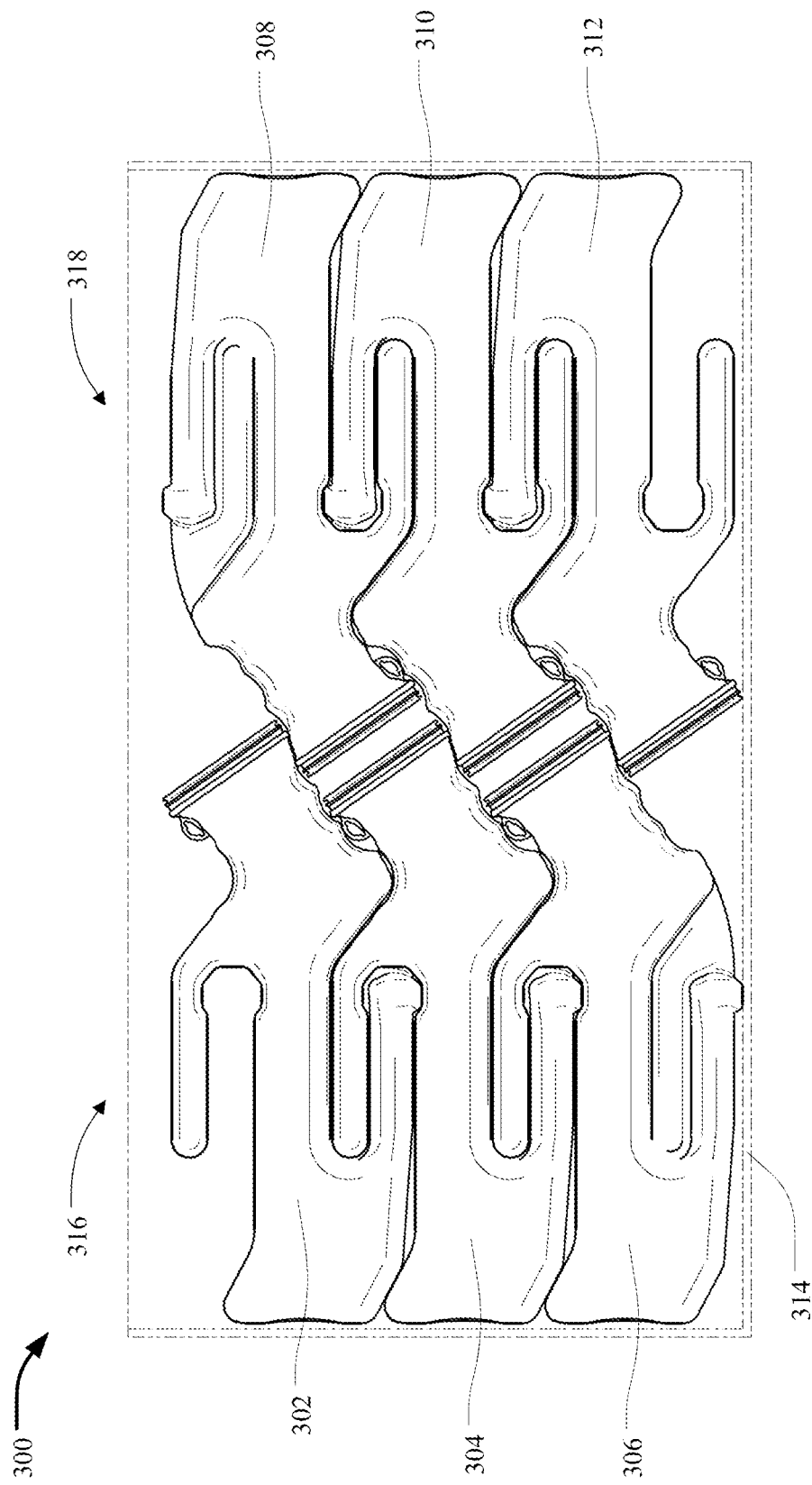
FIG. 11 shows a side view of a urinal system, with multiple urinals stacked together that illustrate the nesting engagement between adjacent urinals.

FIG. 11 shows a side view of a urinal system 300 with multiple urinals stacked together that illustrate the nesting engagement between adjacent urinals. For example, the urinal system 300 can include urinals 302, 304, 306, 308, 310, 312, that can be positioned within a container 314. Each urinal 302, 304, 306, 308, 310, 312 can be implemented in a similar manner as the other urinals described herein (e.g., the urinal 100). In addition, while six urinals 302, 304, 306, 308, 310, 312 are illustrated being positioned within a container 314, the urinal system 300 can include other numbers of urinals (e.g., two, three, four, greater than six, etc.). As shown in FIG. 11, two or more of the urinals 302, 304, 306 can define a first column of urinals 316, and two or more of the urinals 308, 310, 312 can define a second column of urinals 318. Each urinal of the first column of urinals 316 can be oriented the same in a first orientation, while each urinal of the second column of urinals 318 can be orientated the same in a second orientation. However, the first orientation can be different than the second orientation. For example, the first orientation can be inverted relative to the second orientation. In this way, the first column of urinals 316 can be inverted relative to the second column of urinals 318 (e.g., with the first column of urinals 316 and the second column of urinals 318 being positioned within the container 314). In some non-limiting examples, including when stacked, openings of some urinals can be aligned with openings of other urinals. For example, the opening of the urinal 304 can be aligned with the opening of the urinal 308, the opening of the urinal 306 can be aligned with the opening of the urinal 310, and so on.

As shown in FIG. 11, the first column of urinals 316 are stacked with adjacent urinals being nested within each other. For example, the handle of the urinal 304 can be inserted into the recess of the urinal 302, and the handle of the urinal 306 can be inserted into the recess of the urinal 304. This nesting arrangement can be followed for each urinal in the first column of urinals 316. As shown in FIG. 11, when the handle of the urinal 304 is inserted into the recess of the urinal 302, at least a portion of the urinal 302 outside of the recess of the urinal 302 contacts the urinal 304 (e.g., a bottom of the urinal 302, the extension of the urinal 302, the neck of the urinal 302, etc., contacts a top of the urinal 304). In some cases, including when the handle of the urinal 304 is inserted into the recess of the urinal 302, the loop of the urinal can be inserted within a first recess of the urinal 302 (e.g., at a neck of the urinal 302), and a portion of the urinal 304 that defines the opening of the urinal 304 can be inserted into a second recess of the urinal 302 (e.g., at the neck of the urinal 302). In some non-limiting examples, the extension (and the ridge of the extension) of the urinal 302 can be inserted into the gap between the handle of the urinal 304 and the body of the urinal 304. In some cases, the ridge of the urinal 302 can interface with a concave region of the urinal 304 (e.g., at the gap of the urinal 304).

In some non-limiting examples, a portion of a urinal from the second column of urinals 318 can interface with a portion of a urinal from the first column of urinals 316 (and vice versa). For example, as shown in FIG. 11, a portion of the urinal 308 at the opening of the urinal 308 (e.g., the mouth of the urinal 308) can be inserted into a third recess of the urinal 302 (e.g., at the neck of the urinal 302), in which the third recess is positioned above the first and second recesses. Correspondingly, a portion of the urinal 304 at the opening of the urinal 304 can be inserted into a recess of the urinal 310 (e.g., that is directed into the neck of the urinal 310, which can be similar to the third recess of the urinal 302). In this way, not only can urinals within a column be nested together to form a compact stack or urinals, but columns of urinals (e.g., stacks of urinals) can also be nested together with other stacks of urinals. Thus, the nestable, stackable, etc., urinals described herein can considerably improve the packing efficiency within a container (e.g., the container 314). For example, in some cases, 33% more urinals can be packed within the same volume of a container as compared to typical urinals (e.g., urinals with a centrally located handle).

Figure 12:
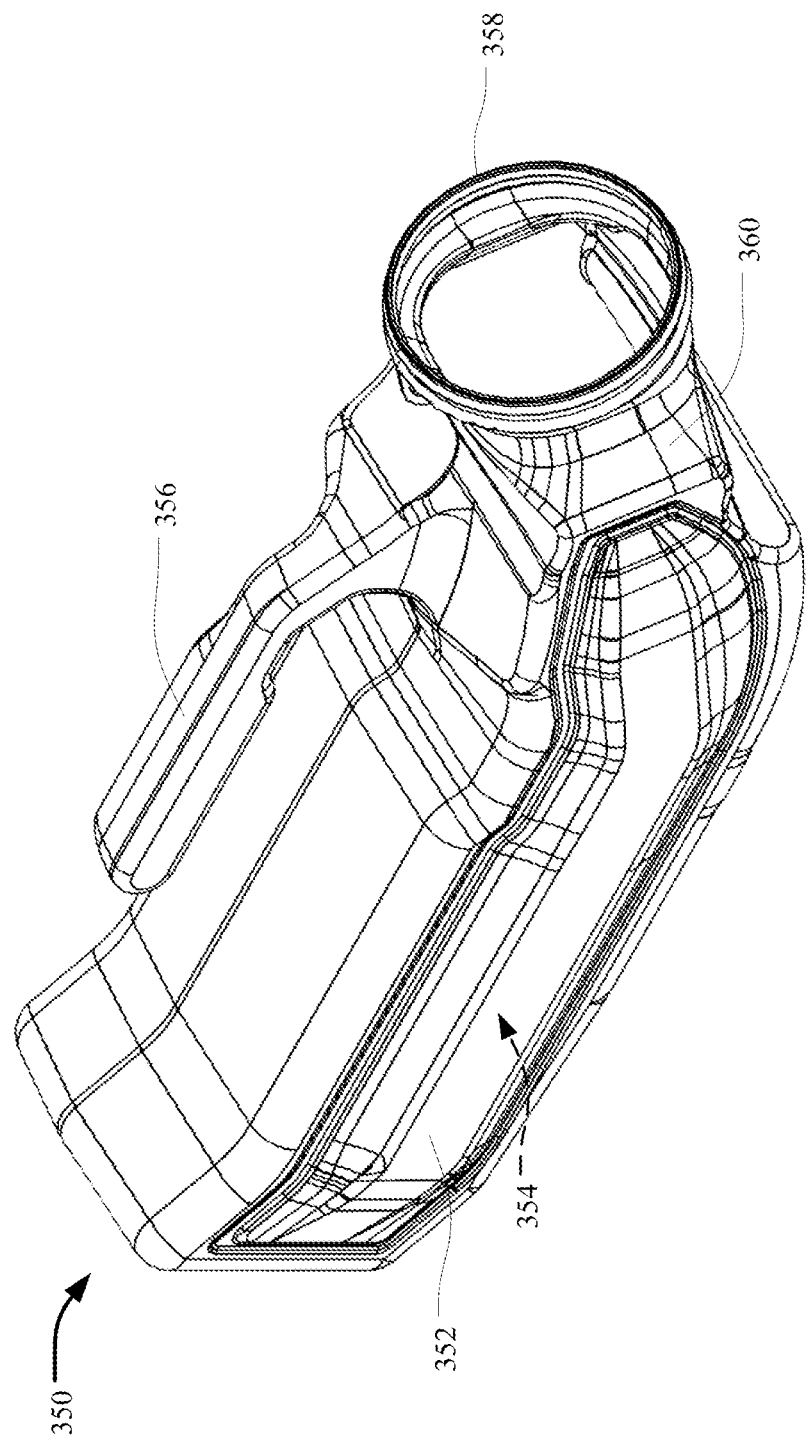
FIG. 12 shows a front isometric view of another urinal.

FIG. 12 shows a front isometric view of a urinal 350. The urinal 350 can be implemented in a similar manner as the other urinals described herein including the urinal 100. Thus, the description of the urinal 100 pertains to the description of the urinal 350 (and vice versa). For example, the urinal 350 can include a body 352 that defines an interior volume 354, a handle 356 coupled to (or integrally formed with) the body 352, and an opening 358 that can be fluidly coupled to the interior volume 354. The body 352 can include a neck 360 and the opening 358 can be positioned at the neck 360.

Figure 13:
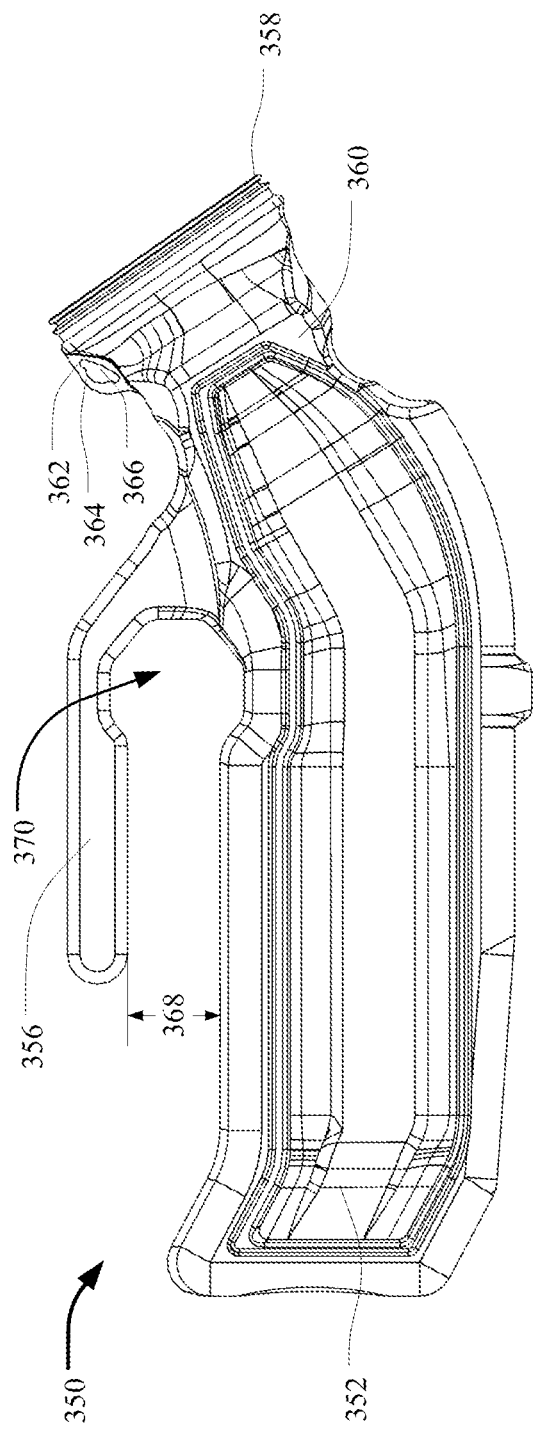
FIG. 13 shows a front side view of the urinal of FIG. 12.

FIG. 13 shows a front side view of the urinal 350. As shown in FIG. 13, the urinal 350 can include a loop 362 that can be coupled to (or integrally formed with) the body 352 and can be positioned at the neck 360 on a top side of the body 352 (e.g., opposite to one or more recesses directed into the neck 360). However, the loop 362 of the urinal 350 (as opposed to the loop 148 of the urinal 100) can include a portion 364 that can be straight (e.g., the portion 364 extending in a straight line). In some cases, the portion 364 can be substantially perpendicular to a plane that defines the opening 358, such that an axis that is parallel to the portion 364 intersects the plane defined by the opening 358 (e.g., with the opening 358 being circular). In some configurations, and similarly to the urinal 100, the loop 362 can define a slot 366, which can be configured to receive a tether (e.g., coupled to a cap that engages with the body 352 of the urinal 350 at the opening 358). The slot 366 can also be straight (e.g., extend in a straight line) and can be angled relative to the portion 364. In some cases, the portion 364 being straight rather than convex can allow for easier engagement between a tether and the loop 362 at the slot 366 (e.g., with the loop 362 less likely blocking a tether as a convex loop such as the loop 148). In addition, the portion 364 having a straight line of sight to the top of the rim aides in automatically assembling, as the end of arm tooling will not have to manipulate the tether in the process of inserting the spade into the loop 362.

As shown in FIG. 13, the urinal 350 can also include a gap 368 between the handle 356 and the body 352 (e.g., at a top surface of the body 352). In some cases, the gap 368 can be defined between a surface of the handle 356 that is straight and a surface of the body 352 that is straight. In some cases, these surfaces can be parallel to each other and each surface that is straight can be parallel to a longitudinal axis of the urinal 350. In some configurations, the gap 368 can also include a concave region 370, which can defined by the body 352, and the handle 356. In some embodiments, the gap 368 (e.g., between the surface of the handle 356 and the surface of the body 352) can be relatively large to accommodate the hands of various practitioners (and users of the urinal 350). Thus, the gap 368 can be substantially (i.e., deviating by less than 10 percent from) 22 millimeters. In some cases, the gap 368 can be greater than 21 millimeters, greater than 25 millimeters, etc. In some configurations, the gap 368 can be used to secure the urinal 350 relative to a bed rail, in which the larger gap 368 can accommodate larger variabilities in bed rails. For example, the bed rail can be inserted into the gap 368 and into the concave region 370 until the bed rail contacts the body 352 of the urinal 350. At this point, the urinal 350 can be supported by the bed rail.

FIG. 14 shows a top view of the urinal 350. As shown in FIG. 14, the handle 356 can decrease in width along the longitudinal axis 372 of the urinal 350 away from the opening 358 (e.g., and towards the rear end of the body 352) to define a decreasing portion and can increase along the longitudinal axis 372 of the urinal 350 away from the opening 358 to define an increasing portion (that is separated from the decreasing portion). For example, the handle 356 can include a base 374, a straight portion 376, and a free end portion 378. The straight portion 376 can be positioned between the base 374 and the free end portion 378. In addition, the base 374 can decrease in width along the longitudinal axis 372 of the urinal 350 away from the opening 358 and the straight portion 376 can be parallel to the longitudinal axis 372. The free end portion 378 can include a portion that increases in width along the longitudinal axis 372 of the urinal 350 away from the opening 358 and a portion that is straight (e.g., and is parallel to the longitudinal axis 372). In some configurations, the portion that is straight of the free end portion 378 can be positioned farther away from the opening 358 than the portion of the free end portion 378 that is straight. In cases, the handle 356 can define a recess 380 that is directed into the handle 356 towards a raised portion 382 of the urinal 350 that is configured to expand (e.g., when compressed). The recess 380 can be concave (e.g., from a top view of the urinal 350 such as the view in FIG. 14) and can define the various portions or segments of the handle 356. In some cases, the width of the free end portion 378 of the handle 356 (e.g., the substantially straight portion thereof) can be larger than the width of the straight portion 376. In this way, a user can more easily insert their hand into around the handle 356 while the larger width of the free end portion 378 can provide a bigger gripping area for better securement (e.g., when holding the urinal 350 by the handle 356). In some configurations, the width of handle 356 and more specifically the width of the free end portion 378 of the handle 356 can be substantially 19 millimeters.

Figure 15:
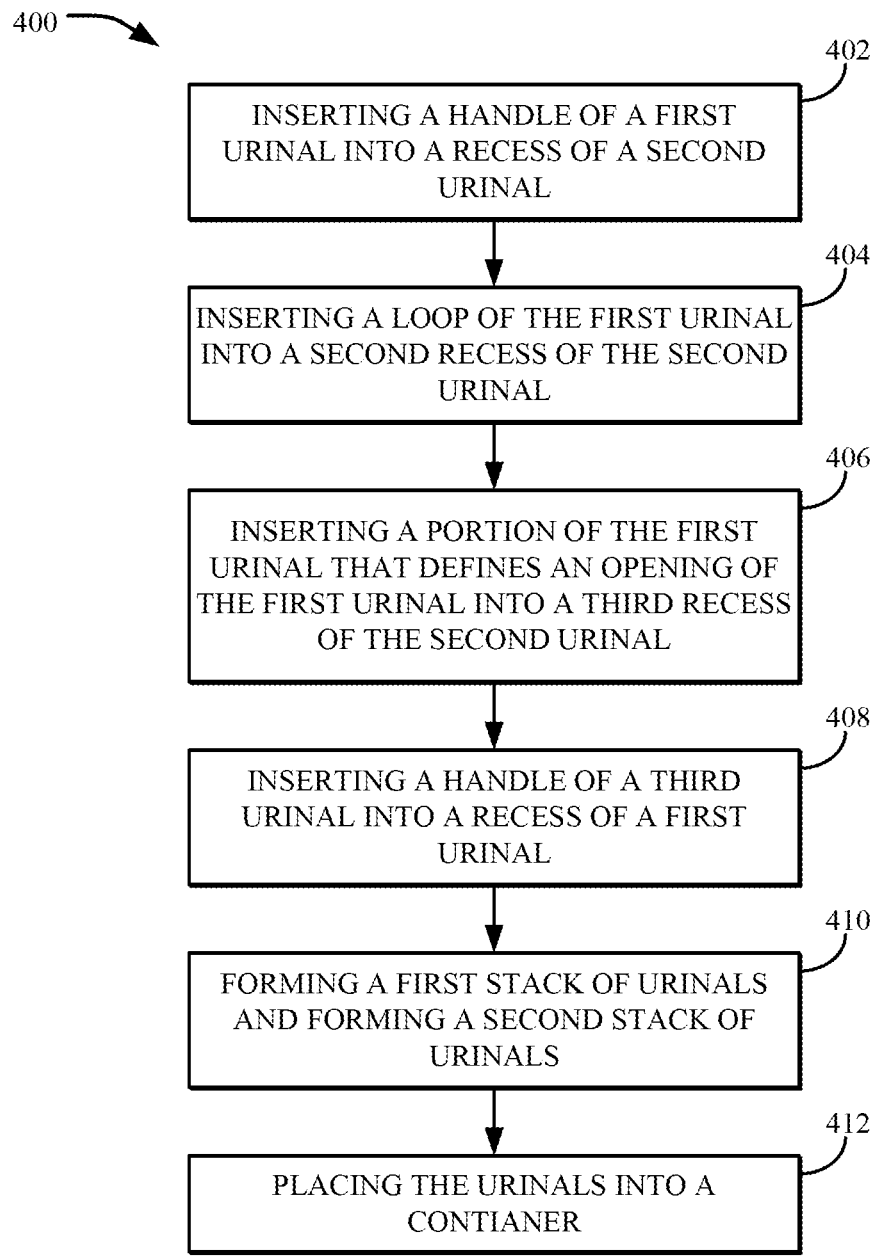
FIG. 15 shows a flowchart of a process of packing urinals.

FIG. 15 shows a flowchart of a process 400 of packing urinals. At 402, the process 350 can include inserting a handle of a first urinal into a recess of a second urinal. In some cases, the recess of the second urinal can be directed into a body of the second urinal (e.g., directed into the bottom end of the body of the second urinal). In some cases, this can include inserting an extension of the second urinal into a gap in the first urinal that is between the handle of the first urinal and the body of the first urinal. In some non-limiting examples, the block 402 can include inserting a base of the handle of the first urinal into a first portion of the recess of the second urinal and inserting an arm of the handle of the first urinal into a second portion of the recess of the second urinal. In some configurations, including after the handle is inserted into the recess, the second urinal can be positioned above the first urinal.

At 404, the process 400 can include inserting a loop of the first urinal into a second recess of the first urinal. In some cases, the loop can be configured to receive a tether (e.g., that is coupled to a cap).

At 406, the process 400 can include inserting a portion of the first urinal that defines an opening of the first urinal into a third recess of the second urinal. In some cases, the third recess can be positioned above the second recess. In some non-limiting examples, the blocks 402, 404, 406 of the process 400 can occur simultaneously. For example, when the handle of the first recess is inserted into the recess of the second urinal, the respective portions of the first urinal can be received within the second urinal.

At 408, the process 400 can include inserting a handle of a third urinal into a recess of the first urinal. In some non-limiting examples, the block 408 can include similar features at the blocks 404, 406, except for the interaction between the first urinal and the third urinal as compared to the second urinal and the first urinal. For example, the block 408 can include inserting a loop of the third urinal into a second recess of the first urinal, inserting a portion of the third urinal that defines an opening of the third urinal into a third recess of the first urinal.

In some non-limiting examples, the process 400 can include forming one or more stacks of urinals (e.g., using some or all of the blocks 402-408), in which each urinal of the stack or urinals has the same orientation (e.g., a first orientation). In some cases, the process 400 can include extending the stack of urinal (e.g., lengthening the stack of urinals) by, for example, using the blocks of the process 350 for additional urinals (e.g., a fourth urinal, a fifth urinal, etc.).

In some non-limiting examples, the block 410 of the process 400 can include forming a first stack of urinals, and a second stack of urinals. In some cases, each urinal of the first stack of urinals can have the same orientation (e.g., a first orientation), and each urinal of the second stack of urinals can have the same orientation (e.g., a second orientation) that is different than the orientation of the urinals of the first stack of urinals (e.g., inverted). In some cases, this can include inverting the second stack of urinals to an inverted orientation relative to the first stack or urinals. In some cases, this can include aligning an opening of one or more urinals of the first stack of urinals with a respective opening of one or more urinals of the second stack of urinals. In some non-limiting examples, the process 350 can include inserting a portion of a fourth urinal that defines an opening of the fourth urinal into a fourth recess of the second urinal (e.g., in which the fourth recess is positioned above the second recess and the third recess).

At 412, the process 400 can include placing the multiple urinals (e.g., including the first stack or urinals, the second stack of urinals, etc.), into a container. In some cases, this can include decreasing an internal volume of each urinal of the multiple urinals (e.g., which can include decreasing the internal volume of one urinal). For example, this can include compressing a raised portion of a urinal to decrease the internal volume of the urinal (e.g., for each urinal of the plurality of urinals). In some cases, this can include contacting the raised portion of the urinal with an adjacent urinal (e.g., a substantially flat portion of the adjacent urinal opposite a raised portion of the adjacent urinal) to compress the raised portion of the urinal.

The present disclosure has described one or more preferred non-limiting examples, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the accompanying description or illustrated in the accompanying drawings. The disclosure is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular non-limiting examples or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or non-limiting examples. Further, references to particular rotational or other movements (e.g., counterclockwise rotation) is generally intended as a description only of movement relative a reference frame of a particular example of illustration.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the disclosure. Further, in some non-limiting examples, certain operations can be executed in parallel, including by dedicated parallel processing devices, or separate computing devices configured to interoperate as part of a large system.

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as non-limiting examples of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use non-limiting examples of the disclosure. Various modifications to the illustrated examples will be readily apparent to those skilled in the art, and the generic principles herein can be applied to other examples and applications without departing from the principles disclosed herein. Thus, non-limiting examples of the disclosure are not intended to be limited to non-limiting examples shown but are to be accorded the widest scope consistent with the principles and features disclosed herein and the claims below. The accompanying detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Also as used herein, unless otherwise limited or defined, "or" indicates a non-exclusive list of components or operations that can be present in any variety of combinations, rather than an exclusive list of components that can be present only as alternatives to each other. For example, a list of "A, B, or C" indicates options of: A; B; C; A and B; A and C; B and C; and A, B, and C. Correspondingly, the term "or" as used herein is intended to indicate exclusive alternatives only when preceded by terms of exclusivity, such as "either," "one of," "only one of," or "exactly one of." Further, a list preceded by "one or more" (and variations thereon) and including "or" to separate listed elements indicates options of one or more of any or all of the listed elements. For example, the phrases "one or more of A, B, or C" and "at least one of A, B, or C" indicate options of: one or more A; one or more B; one or more C; one or more A and one or more B; one or more B and one or more C; one or more A and one or more C; and one or more of each of A, B, and C. Similarly, a list preceded by "a plurality of" (and variations thereon) and including "or" to separate listed elements indicates options of multiple instances of any or all of the listed elements. For example, the phrases "a plurality of A, B, or C" and "two or more of A, B, or C" indicate options of: A and B; B and C; A and C; and A, B, and C. In general, the term "or" as used herein only indicates exclusive alternatives (e.g. "one or the other but not both") when preceded by terms of exclusivity, such as "either," "one of," "only one of," or "exactly one of."

Also as used herein, unless otherwise specified or limited, the terms "about" and "approximately," as used herein with respect to a reference value, refer to variations from the reference value of ±15% or less (e.g., ±10%, ±5%, etc.), inclusive of the endpoints of the range. Similarly, the term "substantially equal" (and the like) as used herein with respect to a reference value refers to variations from the reference value of less than ±30% (e.g., ±20%, ±10%, ±5%) inclusive. Where specified, "substantially" can indicate in particular a variation in one numerical direction relative to a reference value. For example, "substantially less" than a reference value (and the like) indicates a value that is reduced from the reference value by 30% or more, and "substantially more" than a reference value (and the like) indicates a value that is increased from the reference value by 30% or more.

Also as used herein, unless otherwise limited or defined, "integral" and derivatives thereof (e.g., "integrally") describe elements that are manufactured as a single piece without fasteners, adhesive, or the like to secure separate components together. For example, an element stamped, cast, or otherwise molded as a single-piece component from a single piece of sheet metal or using a single mold, without rivets, screws, or adhesive to hold separately formed pieces together is an integral (and integrally formed) element. In contrast, an element formed from multiple pieces that are separately formed initially then later connected together, is not an integral (or integrally formed) element.

Various features and advantages of the disclosure are set forth in the following claims.

What is claimed is:

1. A urinal comprising:
    a body defining a front end, a rear end opposite the front end, and an internal volume, the body including an opening fluidly coupled to the internal volume of the body and positioned at the front end of the body;
    a handle integrally formed with the body, the handle having a free end that extends away from the front end of the body towards the rear end of the body; and
    a recess directed into a bottom end of the body, the recess being configured to receive a second handle of a second urinal.

2. The urinal of claim 1, wherein the recess includes a first portion and a second portion, the first portion being positioned closer to the rear end of the body than the second portion; and
    wherein the second handle of the second urinal includes a base and an arm extending away from the base; and
    wherein the first portion of the recess is configured to receive the arm of the second handle and the second portion of the recess is configured to receive the base of the second handle.

3. The urinal of claim 1, wherein an internal volume of the handle is fluidly coupled to the internal volume of the body.

4. The urinal of claim 1, wherein the recess of the urinal corresponds in shape to the second handle of the second urinal; and
    wherein when the second handle of the second urinal is inserted into the recess of the urinal, at least a portion of the urinal outside of the recess is configured to contact the second urinal.

5. The urinal of claim 4, wherein the body includes an extension;
    wherein a free end of the extension extends away from the rear end of the body and towards the front end of the body; and
    wherein the extension at least partially defining the recess of the urinal.

6. The urinal of claim 5, wherein the internal volume of the body extends into the extension to define an extension internal volume; and
    wherein the extension internal volume is configured to contain a liquid.

7. The urinal of claim 4, wherein a longitudinal axis bisects at least a portion of the body to define a first side of the body and a second side of the body, and the longitudinal axis extends through the front end and the rear end of the body; and
    wherein at least a portion of the recess, a portion of the extension, a portion of the handle, or a center of the opening is only positioned on the first side of the body.

8. The urinal of claim 7, wherein the portion of the recess, the portion of the extension, the portion of the handle, and the center of the opening is only positioned on the first side of the body.

9. The urinal of claim 8, wherein the entire handle, and the entire recess are positioned on only the first side of the body.

10. The urinal of claim 7, wherein the body includes a seam defines a ridge that extends across at least a portion of the body, a portion of the handle, a portion of the body at the opening, a portion of the extension, a portion of the body at the recess, and a portion of the body outside of the opening and the recess.

11. The urinal of claim 7, wherein the body includes a neck that joins the opening; and wherein the neck is curved or is angled upwardly relative to the longitudinal axis.

12. The urinal of claim 11, wherein the recess is a first recess and the opening is a first opening;

wherein the neck includes a second recess that is directed into the neck; and wherein the second urinal at a second opening of the second urinal is configured to be inserted within the second recess when the second handle of the second urinal is received within the first recess.

13. The urinal of claim 12, further comprising a third recess directed into the neck, the second recess being positioned above the third recess;

wherein the second urinal includes a loop proximal to the second opening that is configured to receive a tether; and wherein the loop of the urinal is configured to be inserted into the third recess of the urinal when the second handle of the second urinal is received within the first recess.

14. The urinal of claim 11, wherein the rear end of the body is angled upwardly relative to the longitudinal axis of the body.

15. The urinal of claim 1, wherein the body includes a first side wall and a second side wall opposite the first side wall;

wherein the first side wall includes a raised portion and a substantially flat portion;

wherein the raised portion is configured to be compressed to align with the substantially flat portion and decrease the internal volume of the body; and wherein the raised portion is configured to expand from being compressed and extend away from the substantially flat portion to increase the internal volume of the body.

16. The urinal of claim 15, wherein the substantially flat portion surrounds the raised portion.

17. The urinal of claim 15, wherein the raised portion spans at least 50% of the entire area of the first side wall.

18. The urinal of claim 15, wherein the raised portion contours the shape of the body along the body.

19. The urinal of claim 18, further comprising indicia that indicates the amount of liquid positioned within the internal volume of the body of the urinal; and wherein the indicia are positioned on the raised portion.

20. The urinal of claim 1, wherein the front end and the rear end are curved upwardly.

21. The urinal of claim 1, wherein the body includes an extension;

wherein a free end of the extension extends past a center of mass of the urinal when the urinal does not include liquid positioned therein, a center of mass of the urinal when the urinal includes liquid positioned therein, or a centroid of the body of the urinal in a direction from the rear end to the front end of the body.

22. The urinal of claim 1, wherein the body includes an extension and a ridge at a free end of the extension;

wherein the ridge is configured to engage a supporting surface to mitigate tilting of the urinal.

23. The urinal of claim 1, wherein the urinal is formed of a polymer or a plastic.

24. The urinal of claim 23, wherein the polymer or the plastic is transparent or translucent.

25. The urinal of claim 1, wherein the body of the urinal defines multiple walls, and wherein each of the multiple walls of the urinal has a thickness that is less than 5.1 millimeters, or less than 1.3 millimeters.

26. The urinal of claim 1, wherein the urinal that includes the internal volume is configured to contain at least 1000 mL.

27. A urinal system comprising:

a first urinal including a first body, a first handle integrally formed with the first body, and a first recess directed into a bottom end of the first body; and a second urinal including a second body and a second handle integrally formed with the first body, wherein the second handle of the second urinal is inserted into the first recess of the first body of the first urinal; and wherein the first urinal is positioned above the second urinal when the second handle of the second urinal is inserted into the first recess of the first urinal.

28. The urinal system of claim 27, wherein the second urinal includes a second recess directed into a bottom end of the second body, and further comprising:

a third urinal including a third body, and a third handle integrally formed with the third body; and wherein the third handle of the third urinal is inserted into the second recess of the second urinal.

29. The urinal system of claim 27, wherein the first body of the first urinal includes a first extension; and wherein the first extension is inserted into a first gap that is between the first handle and the first body of the first urinal when the second handle is inserted into the first recess of the first urinal.

30. The urinal system of claim 27, wherein the first urinal is in the same orientation as the second urinal when the second handle of the second urinal is inserted into the first recess of the first urinal.

31. A method of packing multiple urinals in a container, the multiple urinals including a first urinal and a second urinal, the method comprising:

inserting a second handle of the second urinal into a first recess of the first urinal, the first recess being directed into a bottom end of a first body of the first urinal; and inserting a first extension of the first urinal into a second gap of the second urinal, the second gap being positioned between the second handle and a second body of the second urinal.

32. The method of claim 31, wherein the multiple urinals include a third urinal, and further comprising inserting a third handle of a third urinal into a second recess of the second urinal, the second recess being directed into a bottom end of a second body of the second urinal.

33. The method of claim 31, further comprising placing the multiple urinals into a container for shipping or storage of the multiple urinals.

34. The method of claim 31, wherein each of the multiple urinals are formed out of a plastic.

* * * * *